(12) United States Patent  
Fukuma et al.

(10) Patent No.: US 6,726,326 B2
(45) Date of Patent: Apr. 27, 2004

(54) OBSERVATION APPARATUS

(75) Inventors: Yasufumi Fukuma, Tokyo (JP); Hidetaka Aeba, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 0 days.

(21) Appl. No.: 10/309,309

(22) Filed: Dec. 4, 2002

(65) Prior Publication Data

US 2003/0128333 A1 Jul. 10, 2003

(30) Foreign Application Priority Data

Dec. 5, 2001 (JP) ......................... 2001-371536

(51) Int. Cl.[7] ................................. A61B 3/10
(52) U.S. Cl. ......................................... 351/216
(58) Field of Search ............................... 351/205, 206, 351/216, 217, 218, 220, 221; 396/72, 73, 79; 359/642, 643, 656, 676, 680, 683

(56) References Cited

U.S. PATENT DOCUMENTS 4,906,078 A * 3/1990 Inabata et al. .............. 359/680
6,229,962 B1 * 5/2001 Imamura ..................... 396/79

* cited by examiner

Primary Examiner—George Manuel
(74) Attorney, Agent, or Firm—Armstrong, Kratz, Quintos, Hanson & Brooks, LLP

(57) ABSTRACT

An observation apparatus capable of removing astigmatism is provided. The observation apparatus includes a variable power lens system (20) located on an observation path of an observation optical system (13a) extending from an objective lens (19) to an imaging lens (22). A portion of the observation optical system which extends from the objective lens (19) to the variable power lens system (20) serves as an observation path through which reflected light fluxes from an eye fundus (Er) of an operating eye (E) are relayed to the variable power lens system (20) as parallel light fluxes. A portion thereof which extends from the variable power lens system (20) to the imaging lens (22) serves as an observation path through which the reflected light fluxes obtained through the variable power lens system (20) are relayed to an eyepiece (26) as parallel light fluxes. An astigmatism canceling optical element (61) for canceling astigmatism power caused when optical members (60) are held against the operating eye (E) is provided in any location on the observation path of the observation optical system (13a) extending from the objective lens (19) to the eyepiece (26).

14 Claims, 28 Drawing Sheets

Amount of defocus

Amount of defocus

OBSERVATION APPARATUS

BACKGROUND OF THE INVENTION

1. Field of the Invention

The present invention relates to an improvement of an observation apparatus such as an operation microscope or a slit lamp.

2. Description of the Related Art

An operation microscope as an observation apparatus as shown in FIG. 1 is known in the prior art. In FIG. 1, reference numeral 1 denotes a support post, 2 denotes a support arm, and 3 denotes a bracket for attaching an operation microscope which is mounted to the end portion of the support arm.

The support arm 2 is composed of an L-shaped arm 4 and an swinging arm 5. The L-shaped arm 4 is attached to the top end portion of the support arm 2 such that it can be horizontally rotated. The swinging arm 5 is biased upward by a spring provided in the inner portion thereof.

An arm 6 which is held so as to be horizontally rotatable and extends downward is provided to the end portion of the swinging arm 5. The bracket 3 is attached to the arm 6.

An operation microscope 10 is attached to the bracket 3. The operation microscope 10 has a body tube 11. An observation optical system is provided in the body tube 11. An eyepiece lens body tube 11' is provided to the body tube 11.

The operation microscope 10 has, for example, an illumination optical system 12 and an observation optical system 13 as shown in FIG. 2. The illumination optical system 12 is composed of an illumination light source 14, a condenser lens 15, an illumination field stop 16, a collimator lens 17, and a prism 18. Reference symbol 18b denotes a reflection surface of the prism 18. Illumination light from the illumination light source 14 is guided to an objective lens 19 used common to the observation optical system 13 via the condenser lens 15, the illumination field stop 16, the collimator lens 17, and the prism 18. Then, it is guided to, for example, an eye fundus Er of an operating eye E so that the eye fundus Er is illuminated. Note that reference symbol Ea denotes a pupil of the operating eye, Eb denotes an iris, and Ec denotes a cornea.

The observation optical system 13 is composed of a right-eye observation optical system 13a and a left-eye observation optical system 13b as shown in FIG. 3. The right-eye observation optical system 13a includes a variable power lens system (zoom lens system) 20 composed of lenses 20a, 20b, 20c, a beam splitter 21, an imaging lens 22, an image erecting prism 23, an interpupillary distance adjustment prism 24, a field stop 25, and an eyepiece 26. Note that reference symbol 2a1 denotes an entrance pupil and 26a denotes an eye point.

Similarly, the left-eye observation optical system 13b includes a variable power lens system (zoom lens system) 30 composed of lenses 30a, 30b, 30c, a beam splitter 31, an imaging lens 32, an image erecting prism 33, an interpupillary distance adjustment prism 34, a field stop 35, and an eyepiece 36. Note that reference symbol 2b1 denotes entrance pupil and 36a denotes an eye point.

The reflected light from the eye fundus Er of the eye to be examined E is guided to an eye of an operator through optical members from the object lens 19 of both the observation optical systems 13a and 13b to the eyepieces 26 and 36 so that the operator observes the eye fundus Er. A portion of the reflected light from the eye fundus Er is split by the beam splitters 21 and 31 and guided to an auxiliary observation optical system 40 for an assistant operator and a TV image pickup system 50.

In FIG. 3, reference numerals 41 and 51 are imaging lenses, 42 and 52 are reflection mirrors, 43 denotes an eyepiece, and 53 denotes a TV camera. The TV camera 53 has a CCD image pickup element as an image receiving means 53a.

As shown in FIG. 4, an exit pupil 18a of the illumination optical system 12 is disposed in proximity to observation paths 2a2 and 2b2 of both the observation optical systems 13a and 13b. In FIG. 4, reference symbol "O" denotes an optical axis of the objective lens 19, O1 denotes an observation optical axis of the left-eye observation optical system 13a, and O2 denotes an observation optical axis of the right-eye observation optical system.

By the way, there is a case where it is desired to observe an eye fundus and its vicinities using such a kind of operation microscope. In such a case, as shown in FIG. 5, optical members such as a prism or lens, contact prism or contact lens (hereinafter referred to as "optical members") 60 are held against the cornea Ec of the eye to be examined E, thereby observing a vicinity portion Er' of the eye fundus Er. In FIG. 5, such optical members 60 having an apical angle θ (for example, 45 degrees) are held against the cornea Ec.

Thus, when such optical members 60 are held against the cornea Ec, the optical axis "O" of the objective lens 19, an illumination optical axis O' of the illumination optical system 12, and the observation optical axes O1 and O2 of both the observation optical systems 13a and 13b are refracted so that the eye fundus vicinity portion Er' of the eye fundus is observed. When the apical angle θ of optical members 60 are varied as appropriate, an observation site of the eye fundus vicinity portion Er' can be changed as appropriate.

However, when the eye fundus vicinity portion Er' is observed using optical members 60, astigmatism and chromatic aberration are caused by a refraction and dispersion action of light. FIG. 6 is a schematic diagram of astigmatism in a state in which optical members 60 are not held against the operating eye E. The abscissa indicates the amount of defocus when a focusing position is assumed as an origin point and defocusing is made forward and backward. The ordinate indicates a size and a shape of a point image Q at positions corresponding to the respective amounts of defocus. When optical members 60 are not held against the cornea Ec, even if the amount of defocus become large relative to the focusing state, the point image Q is kept in substantially a circular shape. In contrast to this, FIG. 7 is a schematic diagram of astigmatism in a state in which optical members 60 are held against the operating eye. The abscissa indicates the amount of defocus when defocusing is caused forward and backward. The ordinate indicates a size and a shape of the point image at positions corresponding to the respective amounts of defocus.

When optical members 60 are held against the cornea Ec, the astigmatism is caused. That is, a position at which the point image Q becomes circular in shape is shifted from the focusing position and it shape transforms from a longitudinal elliptical shape to a transverse elliptical shape via a minimum circle as the focusing state is changed from a focusing position front side to a focusing position back side.

Also, FIG. 8 is a schematic diagram of astigmatism and chromatic aberration in a state in which optical members are not held against the operating eye. The abscissa indicates the amount of defocus when the focusing position is assumed as an origin point and defocusing is caused forward and backward. The ordinate indicates a size and a shape of the point image Q at positions corresponding to the respective amounts of defocus. When optical members 60 are not held against the cornea Ec, even if the amount of defocus become large relative to the focusing state, the point image Q is kept in substantially a circular shape. Also, almost no chromatic aberration whereby an image is separated among R, G, and B is observed. It is observed only slightly as the amount of defocus increases. Thus, almost no practical problem is caused in the case of the observation in the focusing position.

In contrast to this, FIG. 9 is a schematic diagram of astigmatism and chromatic aberration in a state in which optical members 60 are held against the operating eye Ec. The abscissa indicates the amount of defocus when the focusing position is assumed as an origin point and defocusing is made forward and backward. The ordinate indicates a size and a shape of the point image Q at positions corresponding to the respective amounts of defocus. When optical members 60 are held against the cornea Ec, the astigmatism is caused. That is, a position at which the point image Q becomes circular in shape is shifted from the focusing position and its shape transforms from a longitudinal elliptical shape to a transverse elliptical shape via a minimum circle as the focusing state is changed from a focusing position front side to a focusing position back side. In addition, simultaneously, chromatic aberration is caused by a refraction action of optical members 60 even in the focusing position. Here, the chromatic aberration is schematically indicated using three colors of R, G, and B. A color separation direction is a direction in which refractive power of optical members 60 acts, which is the ordinate direction in this example.

Thus, when the chromatic aberration is caused, as shown in FIG. 10, even if the astigmatism is removed, the chromatic aberration is left.

In the case where the astigmatism and the chromatic aberration are caused, when optical members 60 are held against the cornea Ec of the operating eye E and the eye fundus vicinity portion Er' is observed, the eye fundus image appears as being distorted with color separation. Thus, a sharp image of the eye fundus vicinity portion Er' cannot be viewed so that it is hard to operate the eye fundus vicinity portion Er'.

In particular, when operating an eye into which an intraocular lens (IOL) is implanted, the influences of the astigmatism and the chromatic aberration thereof become large. Thus, there is a problem that it is difficult to observe a sharp image of the eye fundus vicinity portion Er'.

Further, the astigmatism is caused also when optical members 60 are held against the cornea of the operating eye E and coagulation therapy of the eye fundus using laser light is conducted.

SUMMARY OF THE INVENTION

Therefore, a first object of the present invention is to provide an observation apparatus capable of removing astigmatism.

A second object of the present invention is to provide an observation apparatus capable of removing chromatic aberration.

A third object of the present invention is to provide an observation apparatus for conducting eye fundus therapy.

According to a first aspect of the present invention, there is provided an observation apparatus, which comprises a variable power lens system and an imaging lens located on an observation path of the observation optical system extending from an objective lens to an eyepiece, in which:

of the observation optical system, an observation optical system extending from the objective lens to the variable power lens system is an observation path for relaying as parallel light fluxes reflected light from an eye fundus of an operating eye to the variable power lens system; and of the observation optical system, an observation optical system extending from the variable power lens system to the imaging lens is an observation path for relaying as parallel light fluxes the reflected light fluxes obtained through the variable power lens system to the imaging lens, characterized in that an astigmatism canceling optical element is provided on the observation path of the observation optical system extending from the objective lens to the eyepiece, for canceling astigmatism power caused when optical members are held against the operating eye.

According to a second aspect of the present invention, there is provided an observation apparatus characterized in that the astigmatism canceling optical element is provided between the variable power lens system and the imaging lens.

According to a third aspect of the present invention, there is provided an observation apparatus characterized in that the astigmatism canceling optical element is provided between the objective lens and the variable power lens system.

According to a fourth aspect of the present invention, there is provided an observation apparatus characterized in that the astigmatism canceling optical element consists of a pair of variable cylindrical lenses that are rotatable relative to each other about an observation optical axis of the observation path, and further includes a correction lens for arbitrarily correcting the amount of positive or negative astigmatism.

According to a fifth aspect of the present invention, there is provided an observation apparatus comprising amount-of-astigmatism-correction automatic changing means capable of correcting astigmatism that changes according to observation magnifications, characterized in that the amount-of-astigmatism-correction automatic changing means includes variable cylindrical lens rotating means for rotating the variable cylindrical lenses, and the variable cylindrical lens rotating means rotates, in order to cancel the astigmatism, the variable cylindrical lenses relative to each other about the observation optical axis in accordance with an amount of astigmatism correction to thereby change power thereof.

According to a sixth aspect of the present invention, there is provided an observation apparatus characterized in that the observation optical system includes image receiving means for receiving reflected light from the eye fundus, the image receiving means being connected with an image processing device, and the amount-of-astigmatism-correction automatic changing means computes the amount of astigmatism correction by analyzing an eye fundus image received on the image receiving means by the image processing device and controls the variable cylindrical lens rotating means to rotate the variable cylindrical lenses in accordance with a computed result.

According to a seventh aspect of the present invention, there is provided an observation apparatus characterized in that:

the observation optical system includes:
  a projection optical system for projecting a pattern image to the eye fundus through the objective lens; and
  image receiving means for receiving reflected light from the eye fundus, which is connected with an image processing device; and
the amount-of-astigmatism-correction automatic changing means computes the amount of astigmatism correction by analyzing a pattern image received on the image receiving means by using the image processing device, and controls the variable cylindrical lens rotating means to rotate the variable cylindrical lenses in accordance with a computed result.

According to an eighth aspect of the present invention, there is provided an observation apparatus characterized in that:
  the amount-of-astigmatism-correction automatic changing means includes a memory for storing the amounts of astigmatism correction corresponding to respective observation magnifications of a prism having a reference apical angle; and
  the amount-of-astigmatism-correction automatic changing means corrects, after once determining the amount of correction corresponding to an observation magnification of optical members having an apical angle different from that of the prism having the reference apical angle, the amounts of correction corresponding to other observation magnifications in accordance with the amounts of correction stored in the memory.

According to a ninth aspect of the present invention, there is provided an observation apparatus characterized by comprising an achromatic optical element having power in a direction for canceling chromatic aberration caused when optical members are held against the operating eye, the achromatic optical element being provided between the variable power lens system and the imaging lens.

According to a tenth aspect of the present invention, there is provided an observation apparatus, which comprises a variable power lens system and an imaging lens located on an observation path of the observation optical system extending from an objective lens to an eyepiece, in which:
  of the observation optical system, an observation optical system extending from the objective lens to the variable power lens system is an observation path for relaying as parallel light fluxes reflected light from an eye fundus of an operating eye to the variable power lens system; and
  of the observation optical system, an observation optical system extending from the variable power lens system to the imaging lens is an observation path for relaying as parallel light fluxes the reflected light fluxes obtained through the variable power lens system to the imaging lens,
  characterized in that an achromatic optical element is provided on the observation path of the observation optical system extending from the objective lens to the eyepiece, for canceling chromatic aberration caused when optical members are held against the operating eye.

According to an eleventh aspect of the present invention, there is provided an observation apparatus characterized in that the achromatic optical element is provided between the variable power lens system and the eyepiece.

According to a twelfth aspect of the present invention, there is provided an observation apparatus characterized in that the achromatic optical element is provided between the objective lens and the variable power lens system.

According to a thirteenth aspect of the present invention, there is provided an observation apparatus, which comprises:
  a variable power lens system and an imaging lens located on an observation path of the observation optical system extending from an objective lens to an eyepiece, in which:
  of the observation optical system, an observation optical system extending from the objective lens to the variable power lens system is an observation path for relaying as parallel light fluxes reflected light from an eye fundus of an operating eye to the variable power lens system;
  of the observation optical system, an observation optical system extending from the variable power lens system to the imaging lens is an observation path for relaying as parallel light fluxes the reflected light fluxes obtained through the variable power lens system to the imaging lens; and
  the observation optical system includes image receiving means for receiving the reflected light from the eye fundus and displaying an eye fundus image, the image receiving means being connected with an image processing device,
  characterized in that the image processing device includes, in order to correct the chromatic aberration caused when optical members are held against the operating eye, chromatic aberration correcting means for correcting chromatic aberration by digitally combining at one point point images that are obtained by separating an image into three colors of R, G, and B on the image receiving means.

According to a fourteenth aspect of the present invention, there is provided an observation apparatus, which comprises a variable power lens system and an imaging lens located on an observation path of the observation optical system extending from an objective lens to an eyepiece, in which:
  of the observation optical system, an observation optical system extending from the objective lens to the variable power lens system is an observation path for relaying as parallel light fluxes reflected light from an eye fundus of an operating eye to the variable power lens system; and of the observation optical system, an observation optical system extending from the variable power lens system to the imaging lens is an observation path for relaying as parallel light fluxes the reflected light fluxes obtained through the variable power lens system to the imaging lens; and
  eye fundus therapy is performed by using an irradiation optical system for irradiating therapeutic laser light,
  characterized in that an astigmatism canceling optical element is provided for canceling astigmatism caused when optical members are held against the operating eye to allow the therapeutic laser light to be irradiated to the eye fundus.

DETAILED DESCRIPTION OF THE PREFERRED EMBODIMENTS

Embodiment 1

Figure 1:
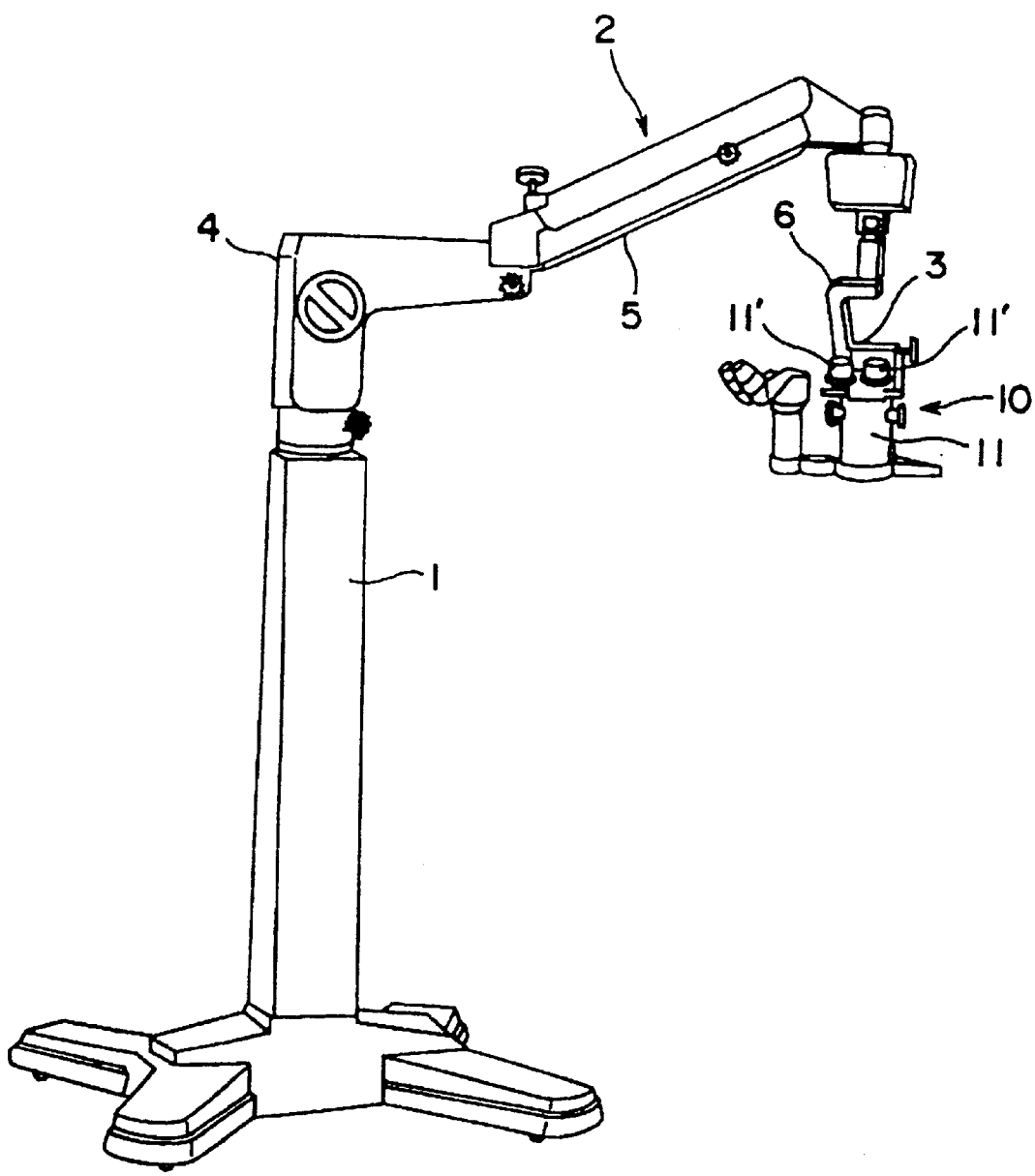
FIG. 1 shows an outline of a conventional operation microscope.
Figure 2:
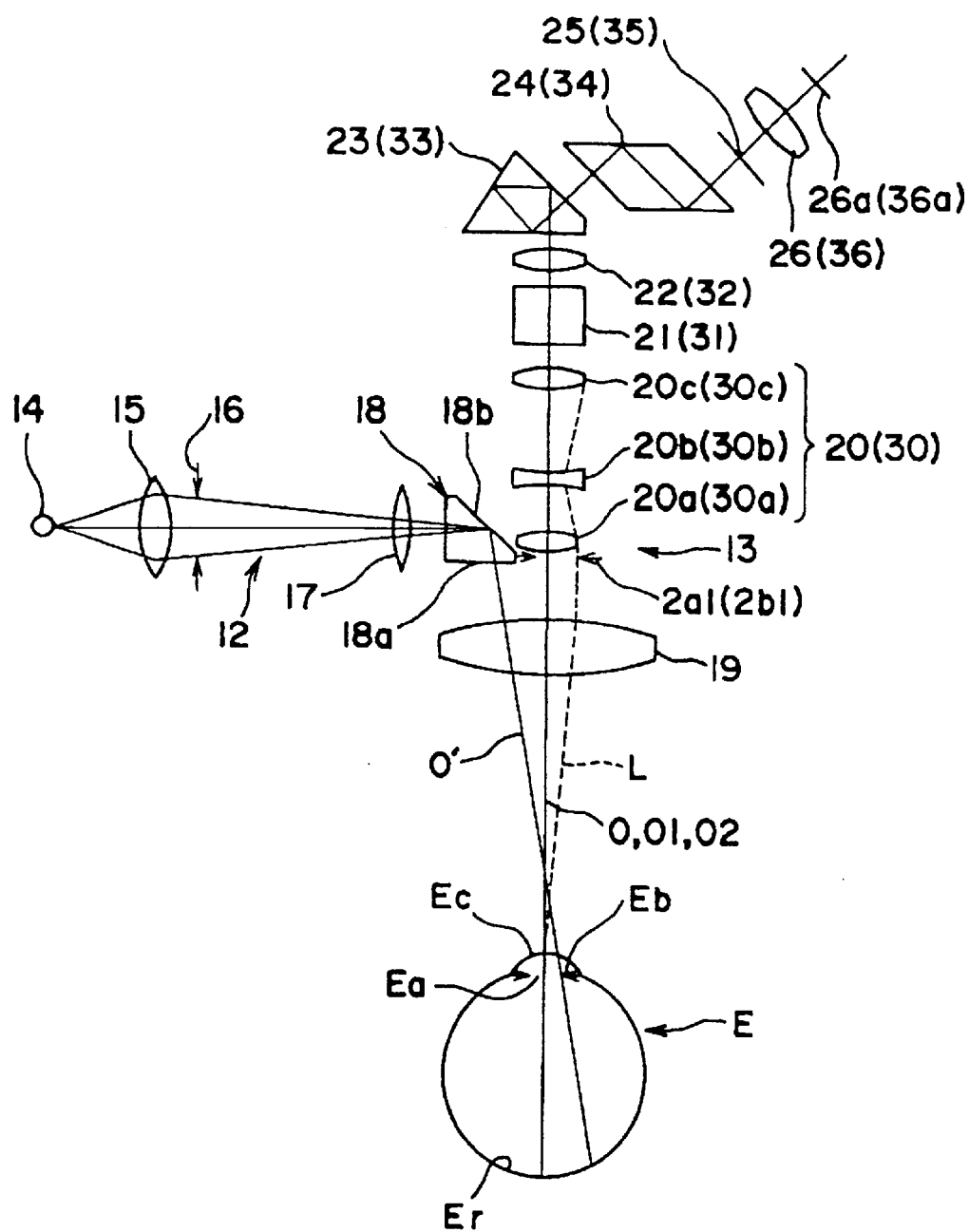
FIG. 2 is a side view showing an outline of a conventional optical system of an operation microscope.
Figure 3:
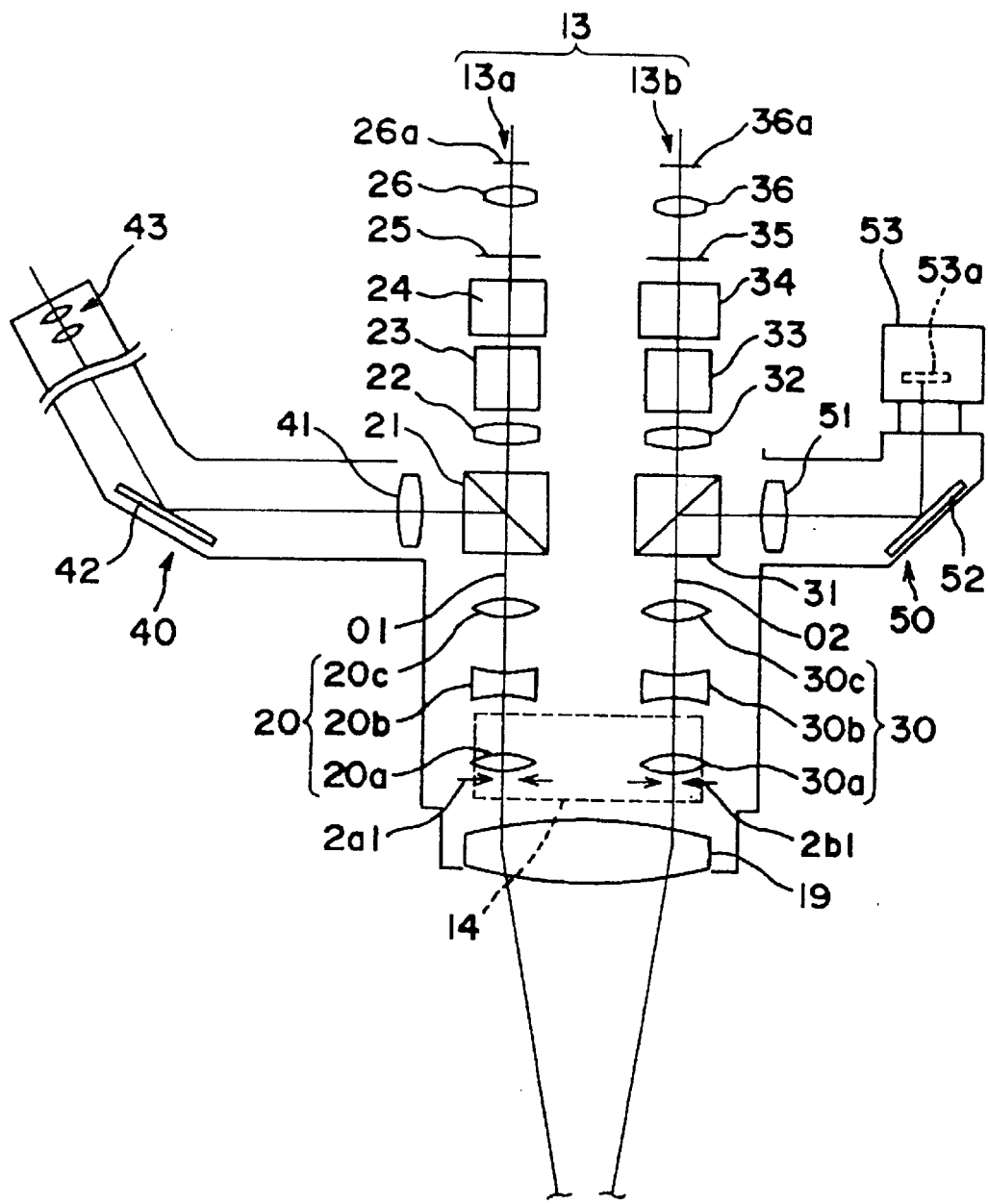
FIG. 3 is a front view showing an outline of the conventional optical system of the operation microscope.
Figure 4:
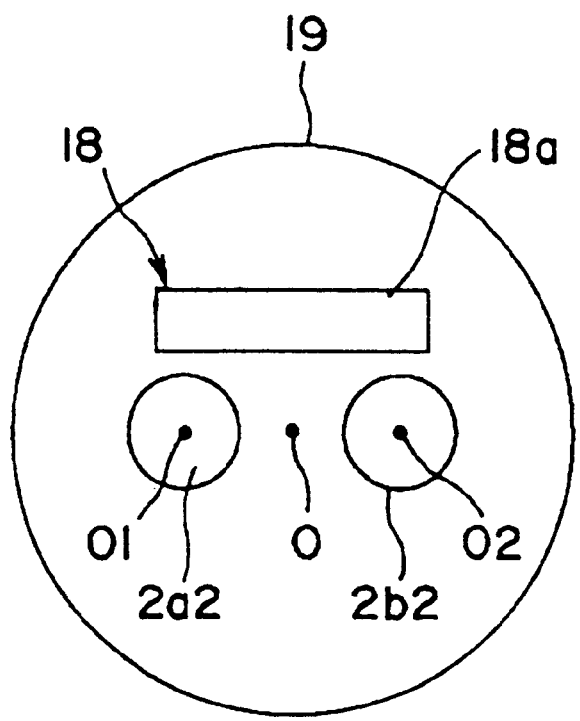
FIG. 4 is a plan view for explaining a relationship between an objective lens and observation paths.
Figure 5:
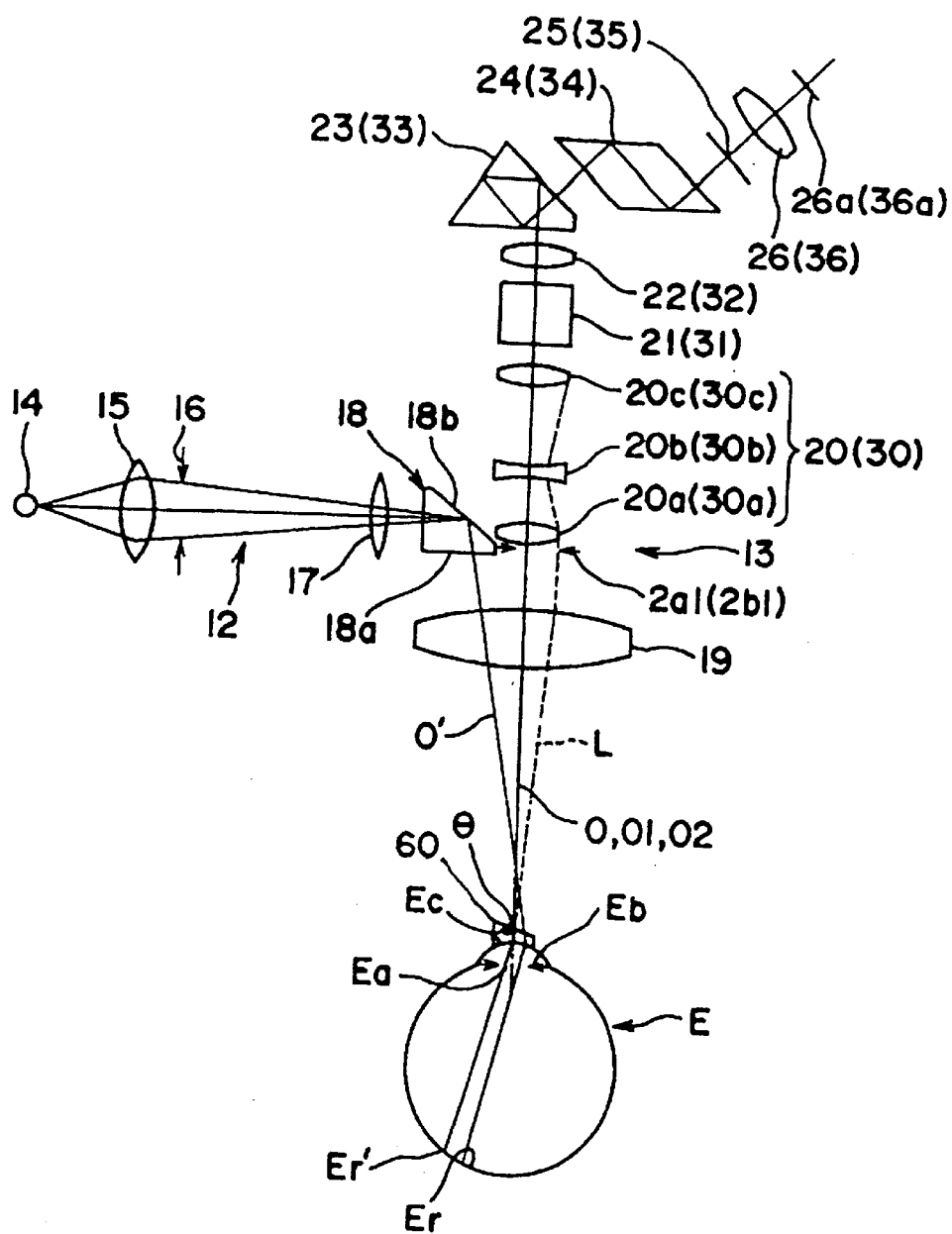
FIG. 5 is an explanatory diagram for explaining a refraction state of an observation optical axis when a contact prism is held against an operating eye.
Figure 11:
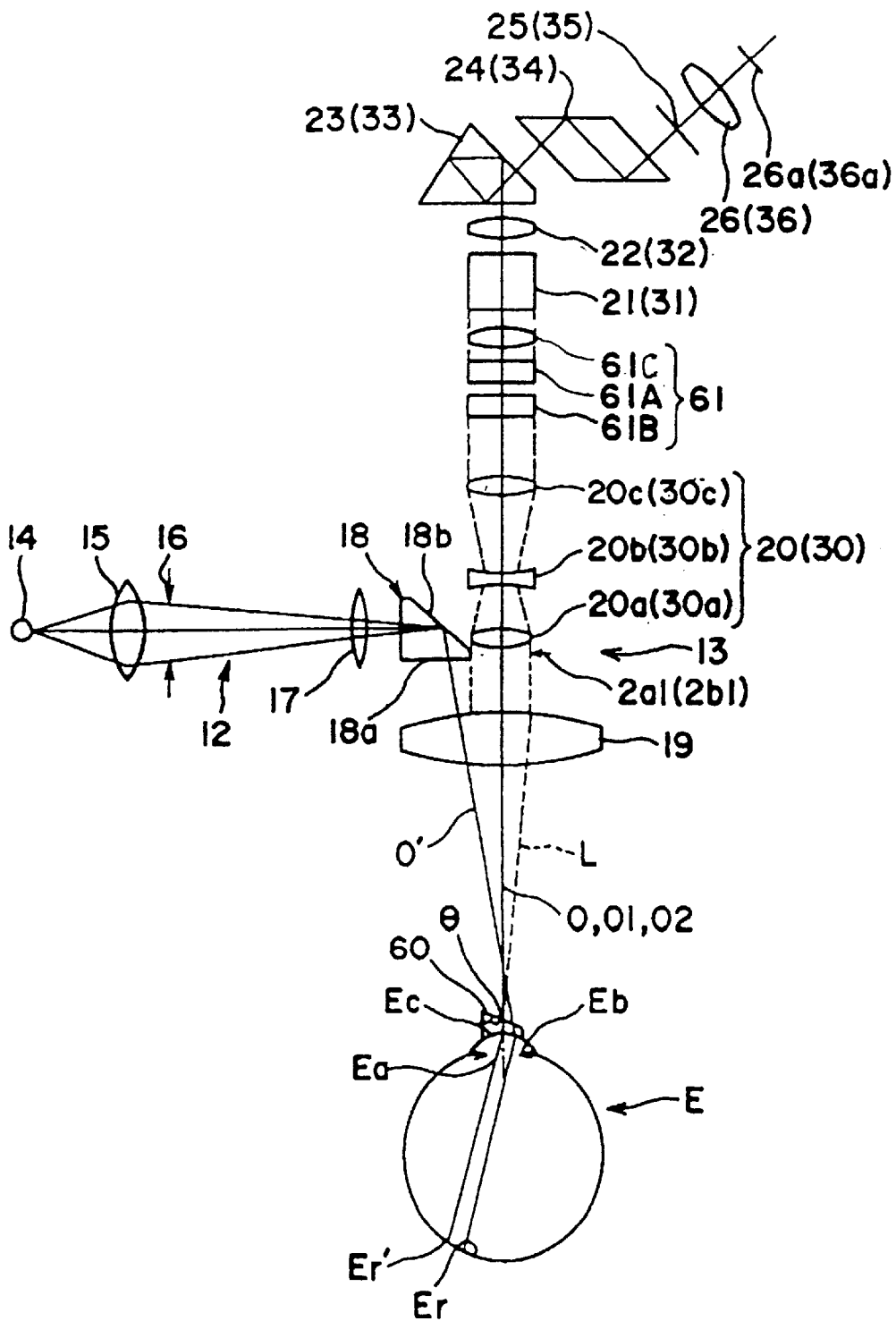
FIG. 11 is a side view showing an optical system of an observation apparatus according to Embodiment 1 of the present invention.
Figure 12:
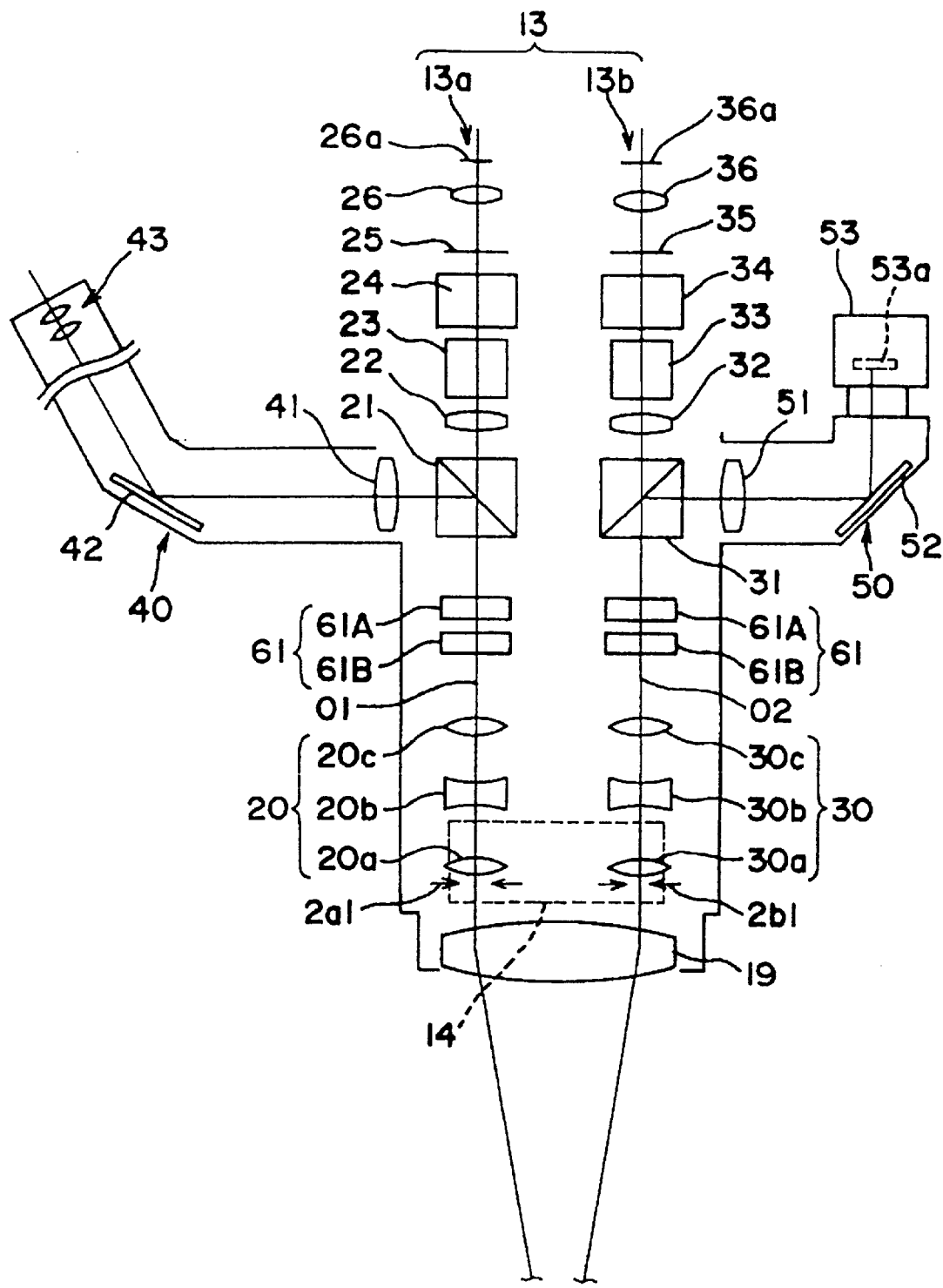
FIG. 12 is a front view showing the optical system of the observation apparatus according to Embodiment 1 of the present invention.

FIGS. 11 and 12 are explanatory diagrams showing an optical system of an observation apparatus according to the present invention. In FIGS. 11 and 12, the same constituent elements as those shown in FIGS. 2 and 3 will be described by designating the same reference symbols thereto, and the description will be mainly focused on other constituent elements.

In both observation optical systems 13a and 13b, an observation path from an objective lens 19 to the variable power lens system 20 (30) serves as an observation path for relaying reflected light fluxes from an eye fundus Er to a variable power lens system 20 (30) as parallel light fluxes. In addition, an observation path from the variable power lens system 20 (30) to the imaging lens 22 (32) serves as an observation path for relaying the reflected light fluxes obtained through the variable power lens system 20 (30) to an imaging lens 22 (32) as parallel light fluxes. Note that reference numeral 26 (36) denotes an eyepiece.

Here, an astigmatism canceling optical element 61 (61) for canceling astigmatism power caused when optical members 60 are held against a cornea Ec of an operating eye E is provided between the variable power lens system 20 (30) and the imaging lens 22 (32). Such position is general as position where an attachment part mounting position of parallel optical system observation apparatus is located.

Figure 13:
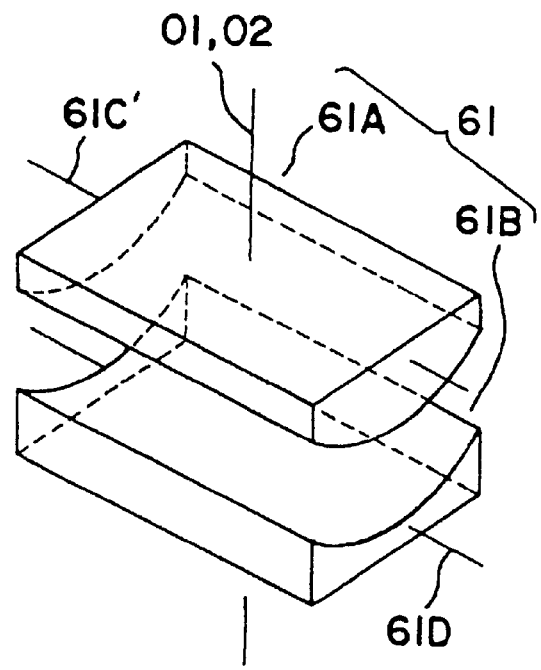
FIG. 13 is a perspective view showing an example of an astigmatism canceling optical element shown in FIGS. 11 and 12 in a state in which power thereof is zero.
Figure 14:
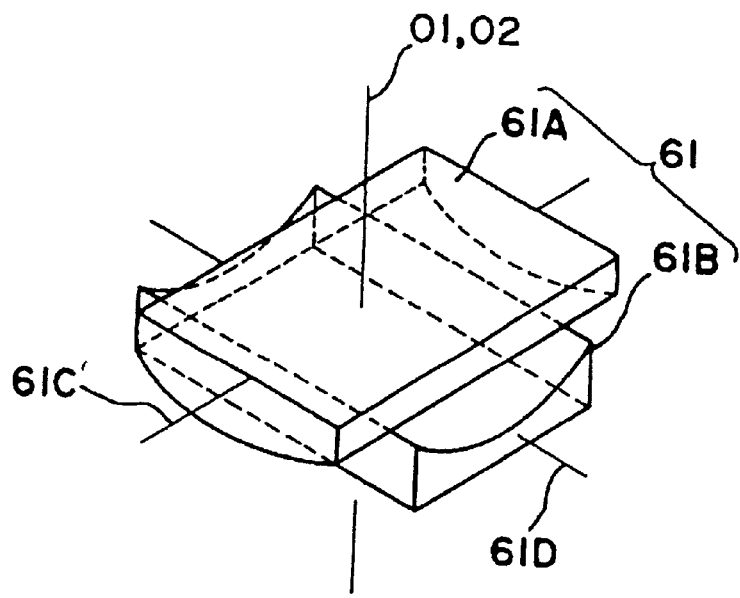
FIG. 14 is a perspective view showing another example of an astigmatism canceling optical element shown in FIGS. 11 and 12 in a state in which power thereof is maximum.

The astigmatism canceling optical element 61 consists of a pair of variable cylindrical lenses 61A and 61B as shown in FIGS. 13 and 14. The variable cylindrical lens 61A is composed of a convex cylindrical lens and the variable cylindrical lens 61B is composed of a concave cylindrical lens.

When a generatrix axis 61C' of the variable cylindrical lens 61A is parallel to a generatrix axis 61D of the variable cylindrical lens 61B, the power is 0 diopters. In addition, when the generatrix axis 61C' of the variable cylindrical lens 61A is orthogonal to the generatrix axis 61D of the variable cylindrical lens 61B, the power becomes maximum.

The variable cylindrical lenses 61A and 61B are located so as to be integrally rotatable about the observation optical axes O1 and O2 and to be rotatable relative to each other. When the variable cylindrical lenses 61A and 61B are integrally rotated about the observation optical axes O1 and O2, the orientation of the astigmatism canceling optical element 61 can be made to correspond to the orientation of the astigmatism caused according to how the optical members 60 are held against the operating eye E. In a state in which the orientation of the astigmatism canceling optical element 61 is kept constant, when either of the variable cylindrical lenses 61A and 61B is relatively rotated to change the power of the astigmatism canceling optical element 61 as appropriate, the astigmatism caused when the optical members 60 are held against the operating eye E can be canceled. In addition, when a power correction lens is changed as appropriate, a sign ("+" or "−") of the caused astigmatism can be arbitrarily controlled.

Figure 15:
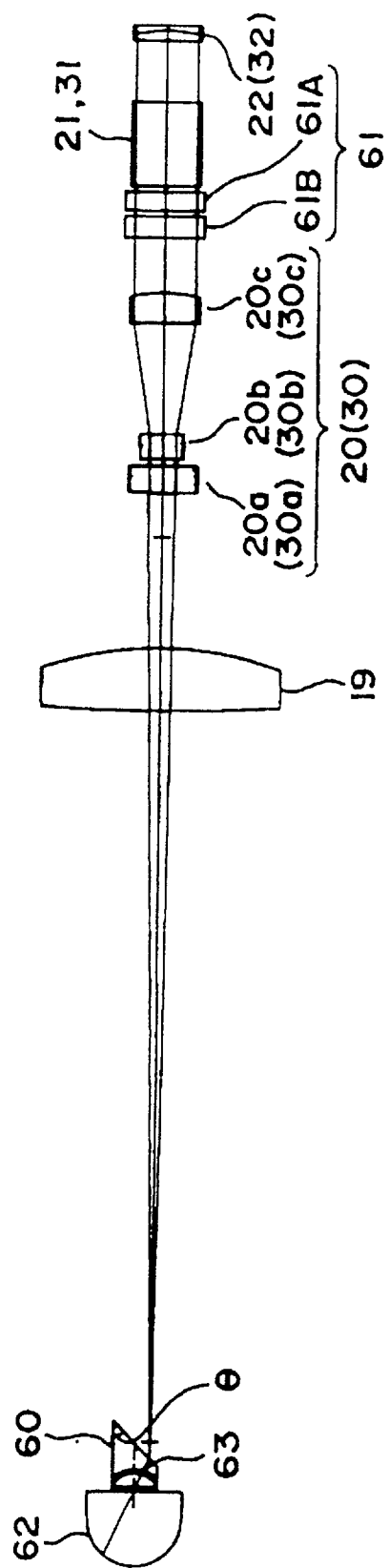
FIG. 15 is a schematic optical configuration diagram for explaining an action of the astigmatism canceling optical element.

FIG. 15 is an explanatory diagram of such an example using a model eye. In FIG. 15, reference numeral 62 denotes a portion of the model eye corresponding to an eye fundus, 63 denotes a portion corresponding to a cornea, and there is shown a state in which the optical members 60 having an apical angle θ of 45 degrees are held against the portion 63 corresponding to a cornea. A focus length f of the objective lens 19 is 200 mm, a focus length f of the imaging lens 22 (32) is 170 mm, and observation magnification by the variable power lens system 20 (30) is 4.2. When the observation magnification is 4.2, the power of the astigmatism canceling optical element 61 which is required for canceling the astigmatism was −0.017 diopters.

Figure 6:
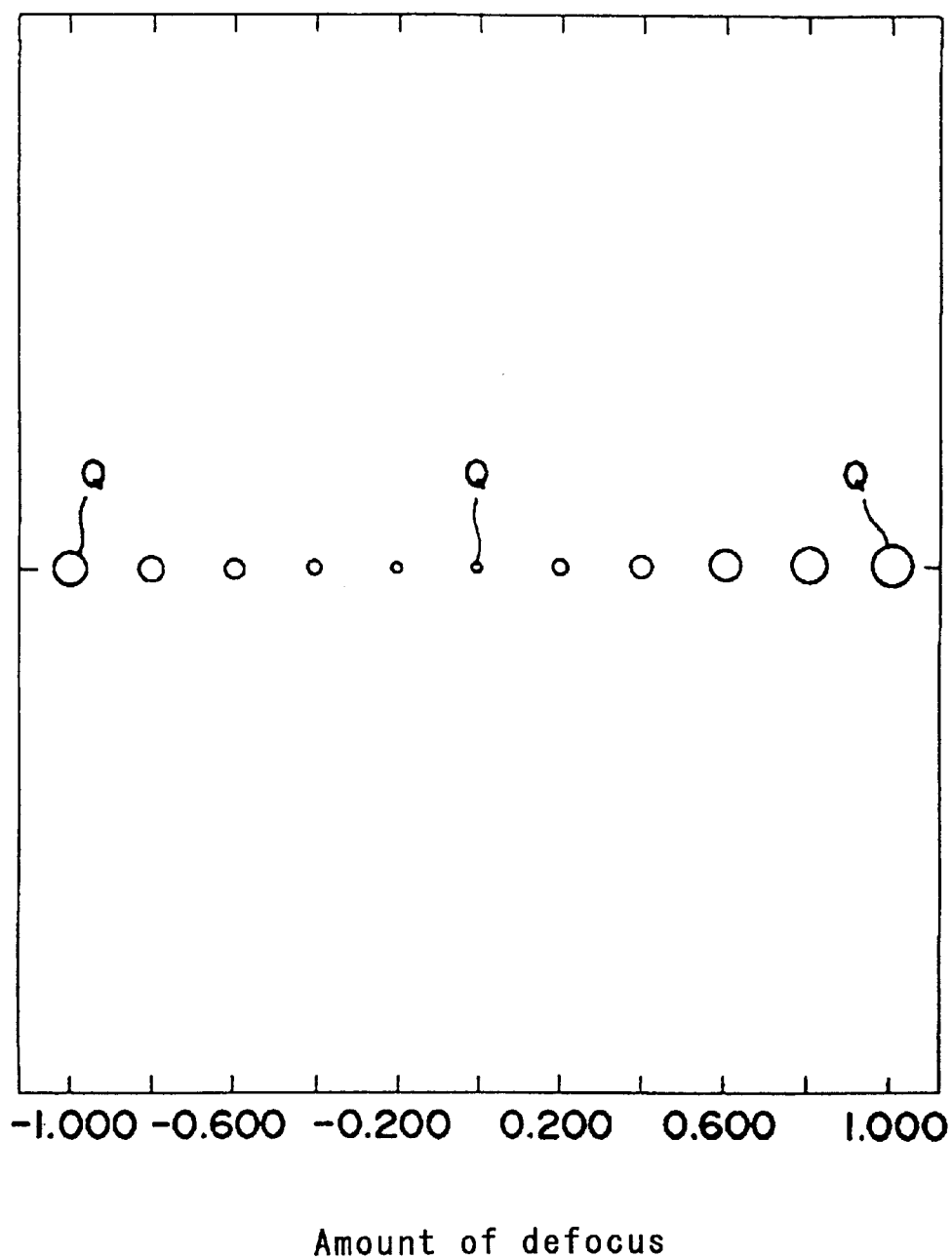
FIG. 6 is an explanatory diagram schematically showing a conventional relationship between the amount of defocus and a point image when it is assumed that no astigmatism is caused.
Figure 7:
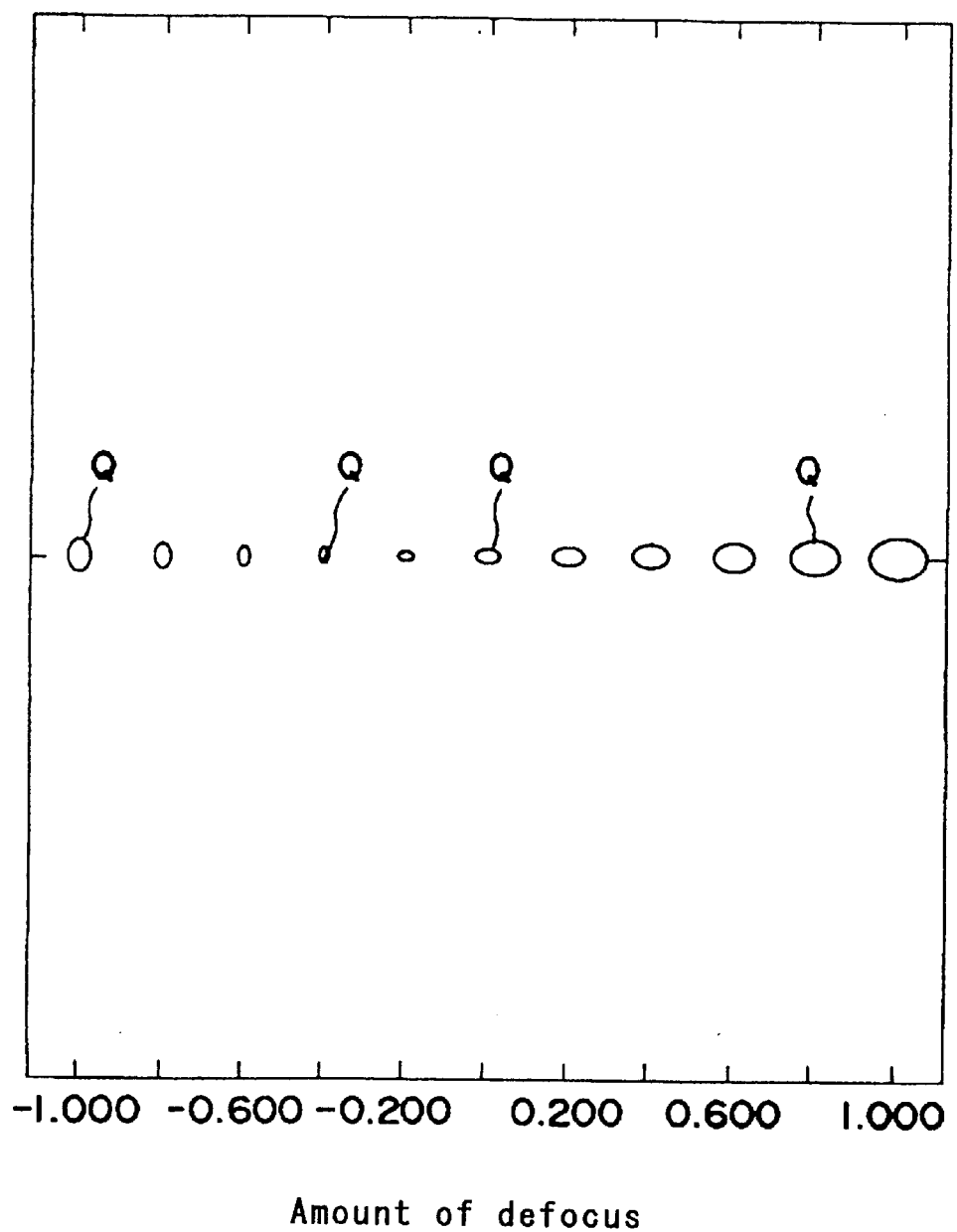
FIG. 7 is an explanatory diagram schematically showing a conventional relationship between the amount of defocus and a point image when it is assumed that astigmatism is caused.

When the astigmatism canceling optical element 61 is not used, the astigmatism is caused as described using FIG. 7. However, when the power is set by using the astigmatism canceling optical element 61 in a direction for canceling the astigmatism, the astigmatism can be canceled as shown in FIG. 6.

When the observation magnification is 6.3, the power of the astigmatism canceling optical element 61 is −0.043 diopters. Similarly, when the observation magnification is 10.5, the power of the astigmatism canceling optical element 61 is −0.11 diopters. When the observation magnification is 16, the power of the astigmatism canceling optical element 61 is −0.284 diopters. When the observation magnification is 21, the power of the astigmatism canceling optical element 61 is −0.445 diopters.

Figure 16:
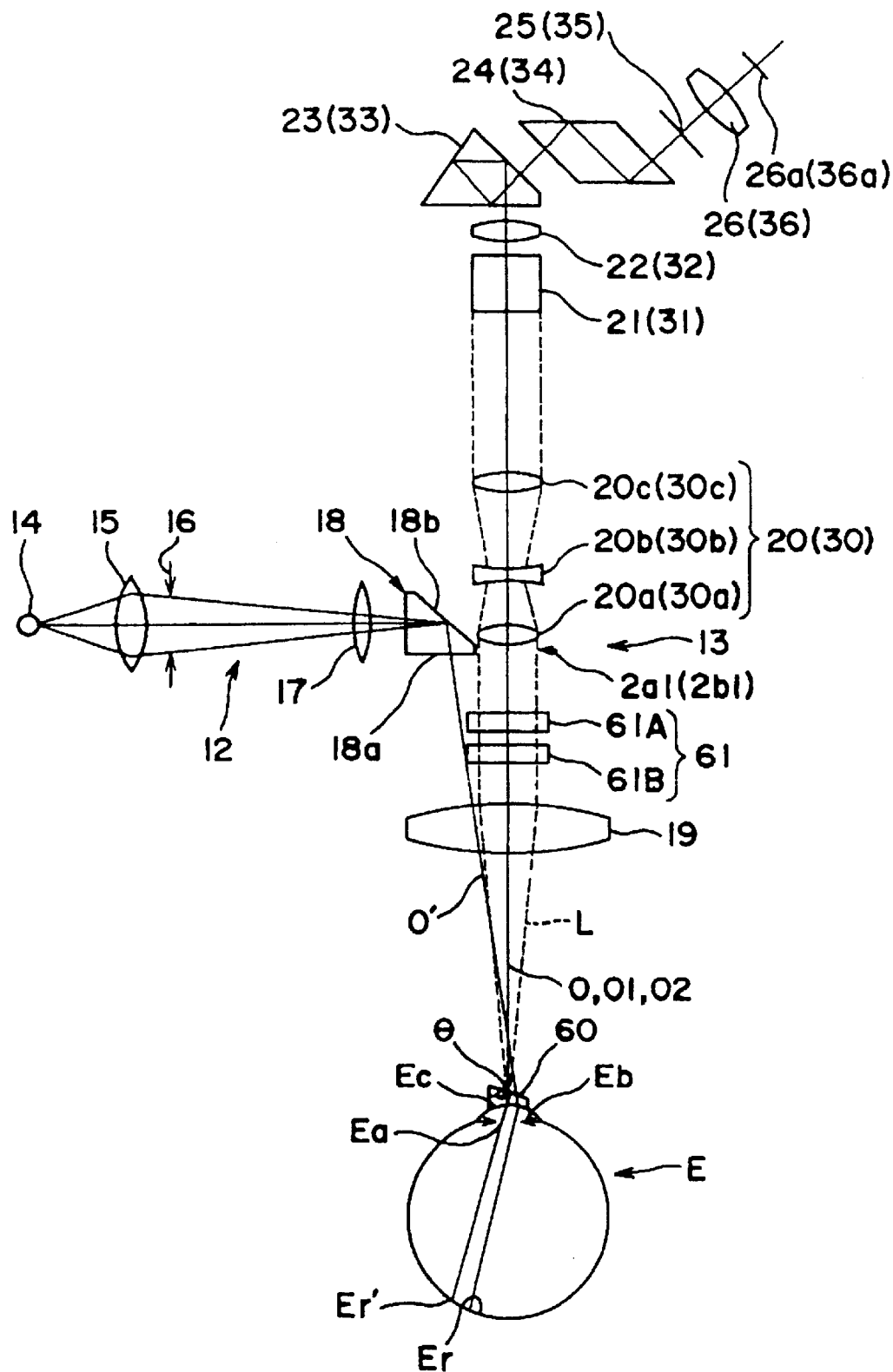
FIG. 16 is a side view showing an optical system of a modified example of an observation apparatus according to the present invention.

FIG. 16 shows a modified example of an observation apparatus according to the present invention. In the modified example, the astigmatism canceling optical element 61 is provided between the objective lens 19 and the variable power lens system 20 (30).

Thus, when the astigmatism canceling optical element 61 is provided between the objective lens 19 and the variable power lens system 20 (30) in a location for relaying reflected light fluxes from the eye fundus Er in parallel, the astigmatism can be canceled without receiving any influence from the variable power and changing the power of the astigmatism canceling optical element 61 according to a change in observation magnification, allowing convenience in operation.

Also, when the astigmatism canceling optical element is provided between the objective lens 19 and the variable power lens system 20 (30) in a location for relaying reflected light fluxes from the eye fundus Er in parallel or in a location for relaying reflected light fluxes obtained through the variable power lens system 20 (30) to the imaging lens 22 (33) in parallel, the astigmatism can be canceled regardless of a distance between the pair of variable cylindrical lenses 61A and 61B so that cancel correction can be easily conducted. Note that it may be provided in any location on the observation path of the observation optical system from the objective lens 19 to the eye piece 26 (36).

Embodiment 2

Figure 17:
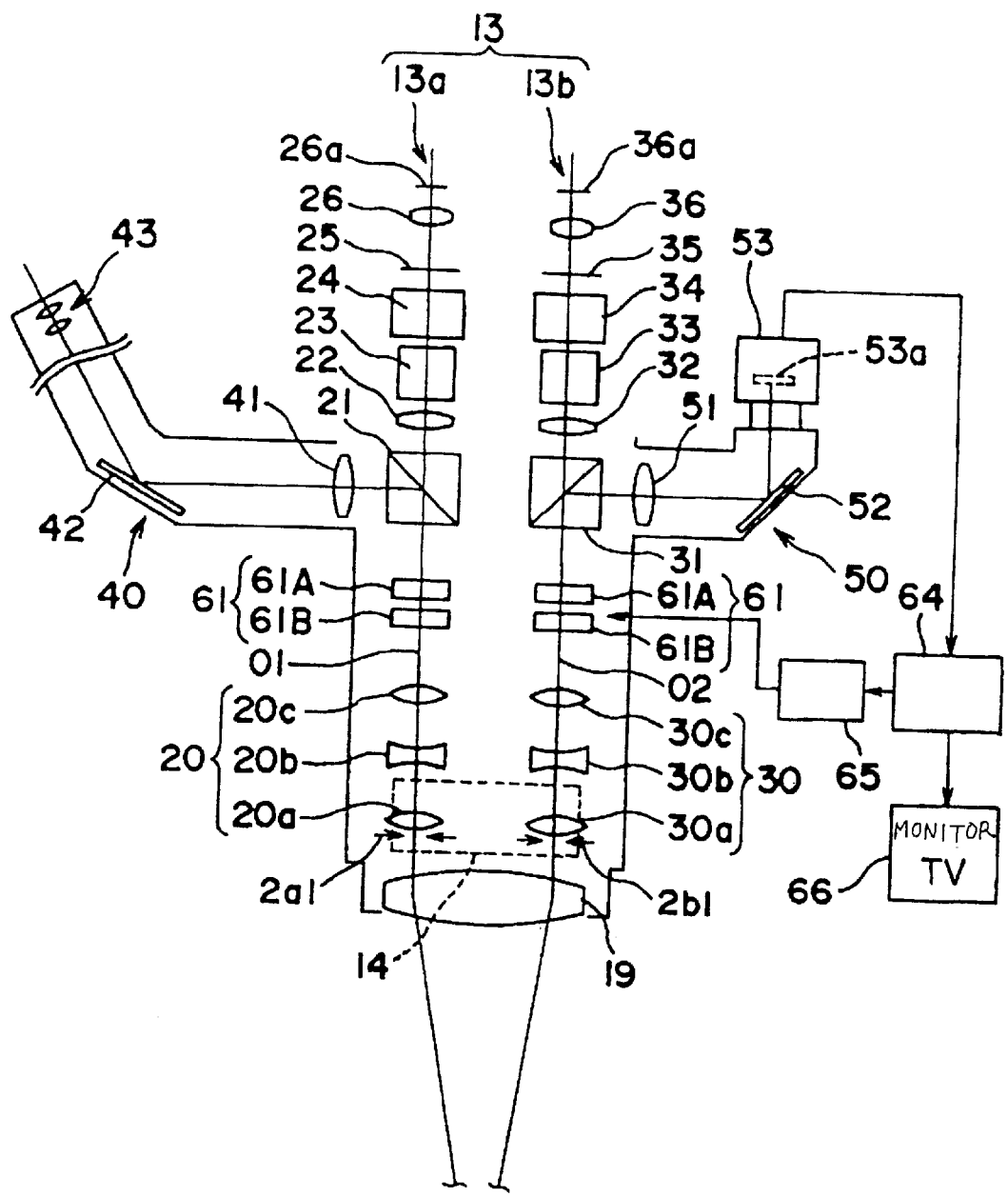
FIG. 17 is a front view showing an optical system of an observation apparatus according to Embodiment 2 of the present invention.

FIG. 17 is an explanatory diagram of an optical system showing Embodiment 2 of an observation apparatus of the present invention. The observation apparatus includes an image processing device 64 and variable cylindrical lens rotating means 65 composing a portion of means for automatically changing the amount of correction for astigmatism. The variable cylindrical lens rotating means 65 includes, for example, a stepping motor. A picture output of a TV camera 53 is inputted to the image processing device 64 and then image data is outputted to a monitor TV 66. The image processing device 64 has an analytical program for correcting astigmatism.

Figure 18:
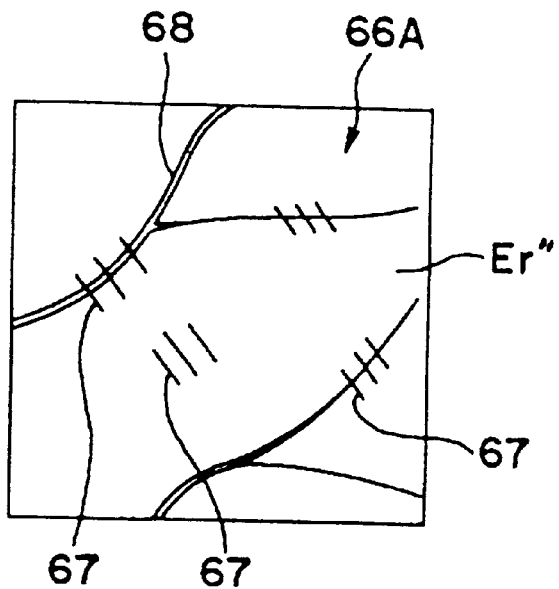
FIG. 18 is a view showing an eye fundus image before astigmatism correction, schematically illustrating a state in which a flow of image resulting from astigmatism occurs on a screen.

As shown in FIG. 18, an eye fundus image Er" of a eye fundus vicinity portion Er' is displayed on a screen 66A of the monitor TV 66. When astigmatism is caused, as schematically shown in the drawing, a flow of image 67 occurs. For example, an image indicating the profile line of a blood vessel 68 appears to flow. The image processing device 64 extracts the image of the blood vessel 68 and outputs a drive signal to the variable cylindrical lens rotating means 65. The variable cylindrical lens rotating means 65 integrally rotates variable cylindrical lenses 61A and 61B in an orientation corresponding to the flow of the profile line.

Figure 19:
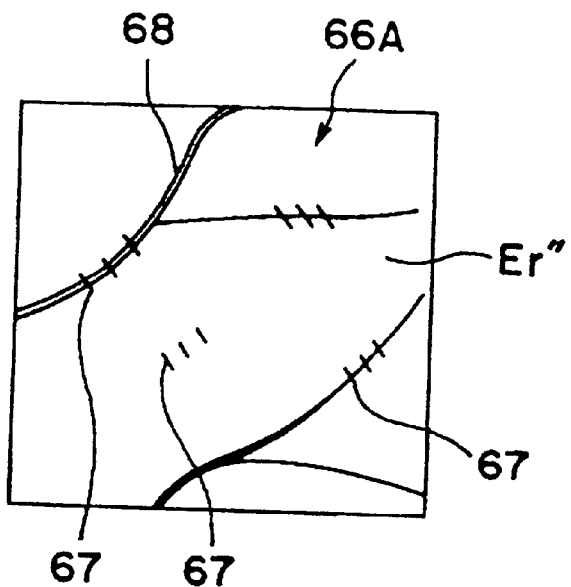
FIG. 19 is a view showing an eye fundus image after astigmatism correction, illustrating a state in which a flow of the eye fundus image is made smaller by correcting the astigmatism.

Next, a generatrix axis of one of the pair of variable cylindrical lenses 61A and 61B is fixed in that orientation. The variable cylindrical lens rotating means 65 relatively rotates the other of the variable cylindrical lenses 61A and 61B according to the magnitude of the flow of the image indicating the profile line. Thus, a diopter with power for canceling astigmatism is set for an astigmatism canceling optical element 61. Then, as shown in FIG. 19, for example, the magnitude of the flow of the image indicating the profile line of the blood vessel 68 becomes smaller. When an eye fundus image in which astigmatism is left is obtained as shown in FIG. 19, the image processing device 64 extracts the image of the blood vessel 68 again and outputs a drive signal to the variable cylindrical lens rotating means 65. The variable cylindrical lens rotating means 65 relatively rotates the variable cylindrical lenses about observation optical axes again according to the magnitude of the flow of the image indicating the profile line to set a diopter with power for canceling astigmatism.

The means for automatically changing the amount of correction for astigmatism relatively rotates the pair of variable cylindrical lenses 61A and 61B until the astigmatism becomes a predetermined amount or less. In addition, positive or negative power is produced by using a correction lens based on a calculated result.

According to Embodiment 2, even when the observation region of the eye fundus vicinity portion Er' is changed using the optical members 60 having a different apical angle θ, the astigmatism can be automatically corrected, thereby obtaining a sharp image of the eye fundus vicinity portion Er'.

Embodiment 3

Figure 20:
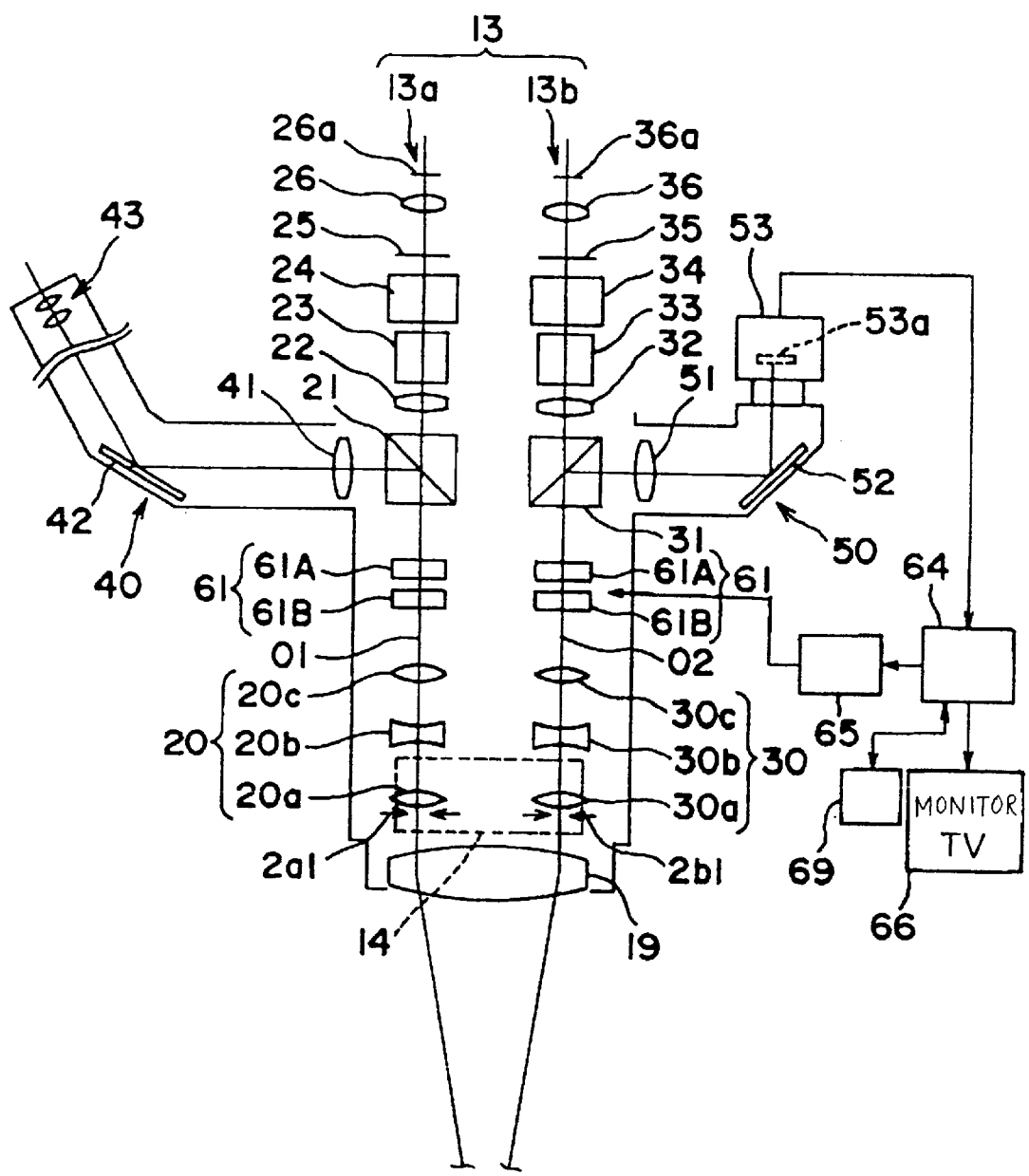
FIG. 20 is a front view showing an optical system of Embodiment 3 of an observation apparatus according to the present invention.

FIG. 20 is an explanatory diagram of an optical system showing Embodiment 3 of an observation apparatus of the present invention. Here, the observation apparatus includes a memory 69.

The memory 69 stores the following amounts of power as correction values. For example, in the case when the optical members 60 having an aptical angle θ of 45 degrees are held against a portion 63 corresponding to a cornea, it stores −0.017 diopters as the amount of power required for an astigmatism canceling optical element 61 in the case where observation magnification is set to 4.2. Similarly, −0.043 diopters is stored as the amount of power required for the astigmatism canceling optical element 61 in the case where observation magnification is set to 6.3. In addition, −0.11 diopters is stored as the amount of power required for the astigmatism canceling optical element 61 in the case where observation magnification is set to 10.5. Further, 0.284 diopters is stored as the amount of power required for the astigmatism canceling optical element 61 in the case where observation magnification is set to 10.5. Furthermore, −0.445 diopters is stored as the amount of power required for the astigmatism canceling optical element 61 in the case where observation magnification is set to 21.

Here, the correction values stored in the memory 69 are used as correction values corresponding to respective observation magnifications of the optical members 60 having a reference apical angle θ. An image processing device 64 includes a computing program for computing the amount of power (the amount of correction) required for canceling astigmatism when the optical members having an apical angle different from the reference apical angle θ of the optical members 60 are held against an operating eye E.

When the optical members having an apical angle different from the reference apical angle θ of the optical members 60 are held against the operating eye E, while observing a screen 66A, an operator first causes the astigmatism canceling optical element 61 to rotate about observation optical axes O1 and O2, thereby setting the amount of power for canceling the astigmatism.

For example, assume a case where the amount of power of the astigmatism canceling optical element 61 which is required for canceling the astigmatism is −0.05 diopters when the optical members 60 having an apical angle θ of 30 degrees are held against the operating eye E and observation magnification is 10.5.

When the operator changes the observation magnification, for example when it is changed from 10.5 to 21, the image processing device 64 reads from the memory 69 a correction value of −0.11 which is a correction value of the optical prism 60 having the reference apical angle θ and obtained in the case where the observation magnification is 10.5 and a correction value of −0.445 which is a correction value of the optical members 60 having the reference apical angle θ and obtained in the case where the observation magnification is 21. Then, the image processing device 64 computes based on the read data a necessary correction ratio corresponding to a multiple of the correction value obtained when the observation magnification is 10.5. Here, the correction ratio is about 4 times.

The image processing device 64 computes based on the correction ratio the amount of correction required for the astigmatism canceling optical element 61 in the case where the optical members 60 having an apical angle θ of 30 degrees are held against the operating eye E and the observation magnification is set to 21.

Variable cylindrical lens rotating means 65 relatively rotates the astigmatism canceling optical element 61 based on the computed result of the amount of correction. Here, the correction ratio is about 4 times. Thus, the astigmatism canceling optical element 61 is rotated such that the amount of power of the astigmatism canceling optical element 61 becomes −0.2 diopters.

According to this Embodiment 3, once the amount of correction corresponding to an observation magnification of a prism having an apical angle different from that of a prism having the reference apical angle is determined, the amounts of correction corresponding to other observation magnifications are corrected according to the amounts of power stored in the memory 69.

Therefore, according to Embodiment 3, the astigmatism can be speedily corrected.

Embodiment 4

Figure 21:
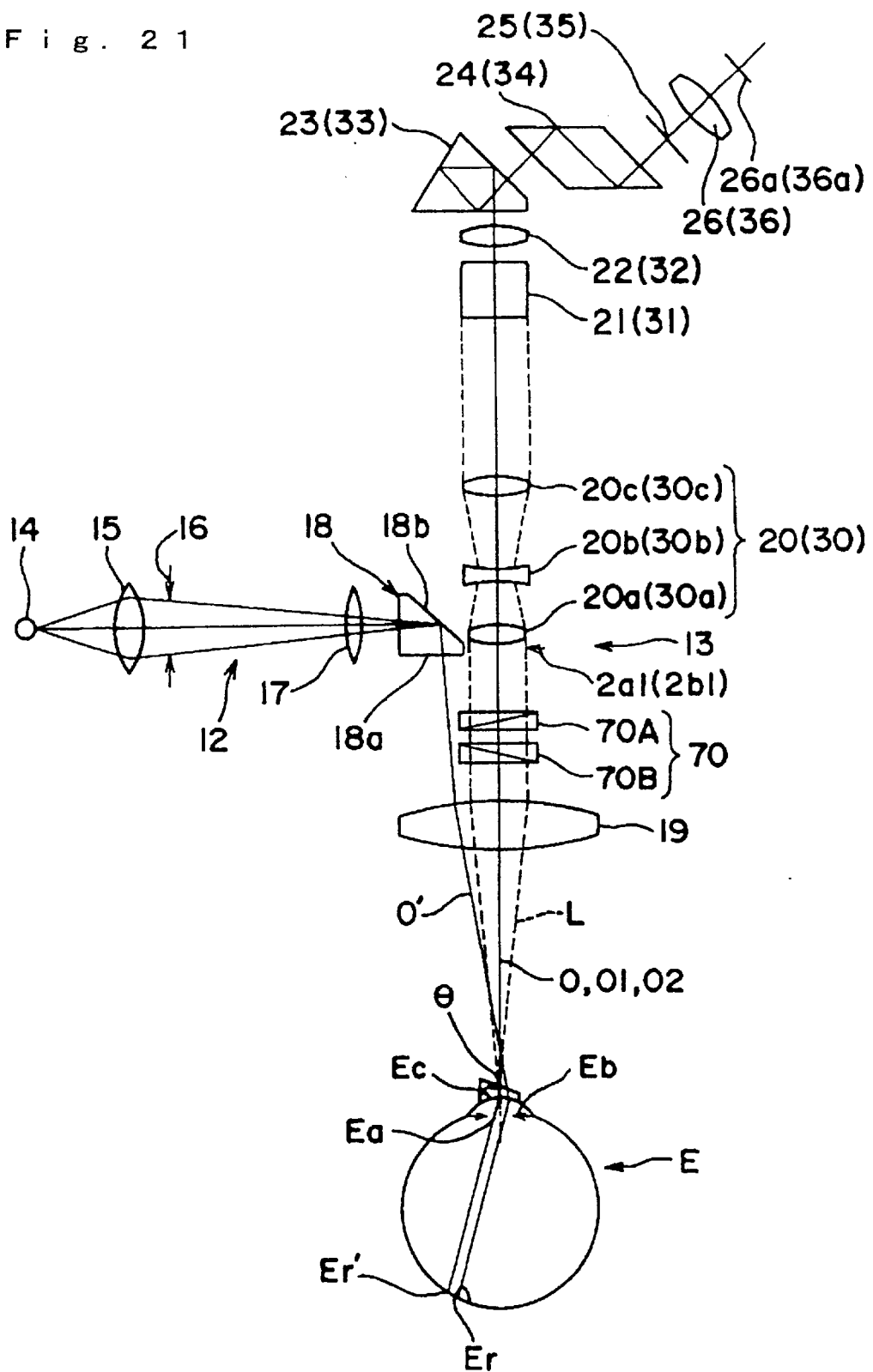
FIG. 21 is a front view showing an optical system of Embodiment 4 of an observation apparatus according to the present invention in a state in which an achromatic optical element is provided to an observation optical system.
Figure 22:
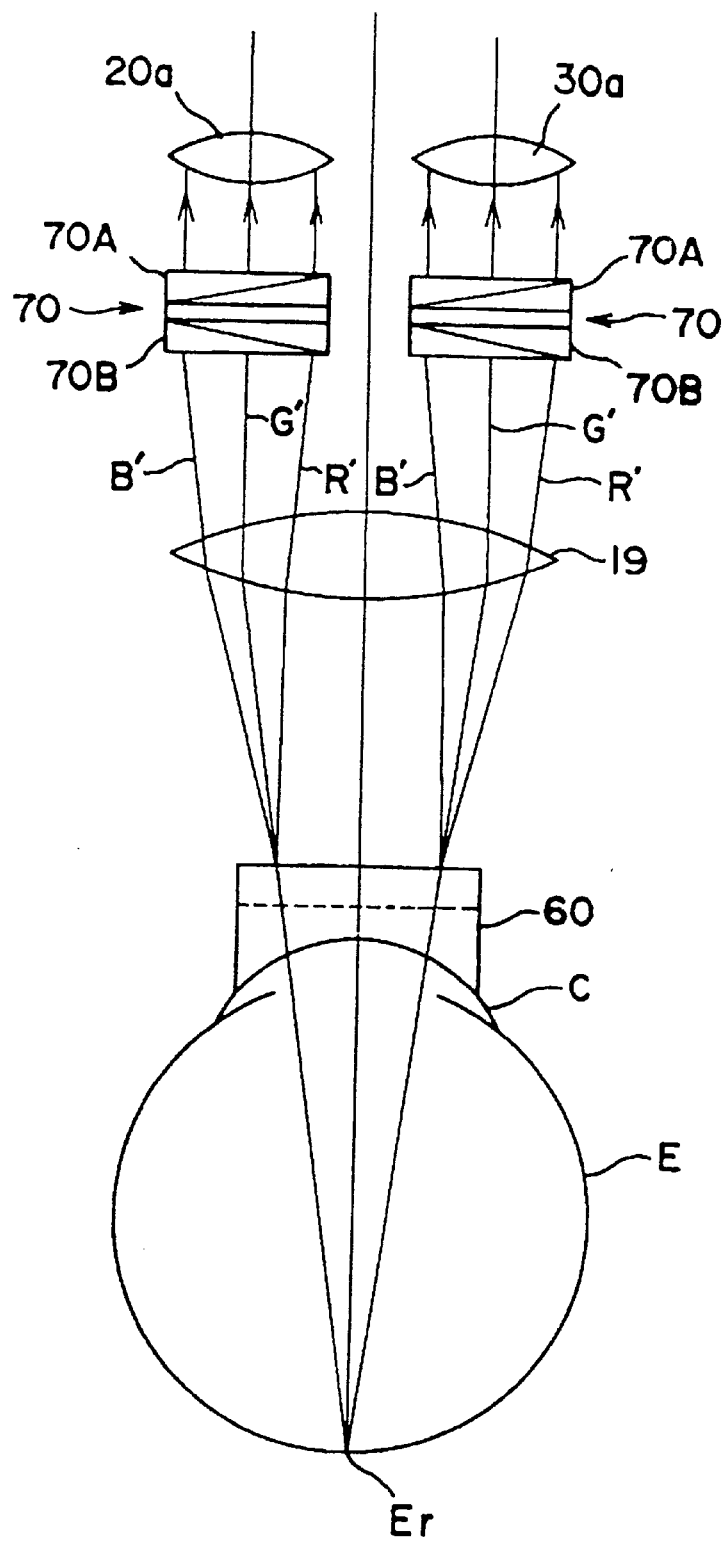
FIG. 22 is an enlarged view showing the portion of the achromatic optical element shown in FIG. 21.

FIGS. 21 and 22 show Embodiment 4 of an observation apparatus according to the present invention, in which a chromatic aberration canceling optical element 70 is provided to each of observation optical systems 13a and 13b.

In this Embodiment 4, the chromatic aberration canceling optical element 70 (70) is provided between an objective lens 19 and a variable power lens system 20 (30) on an observation path for guiding reflected light fluxes from an eye fundus Er of an operating eye E to the variable power lens system 20 (30) as parallel light fluxes.

Figure 23:
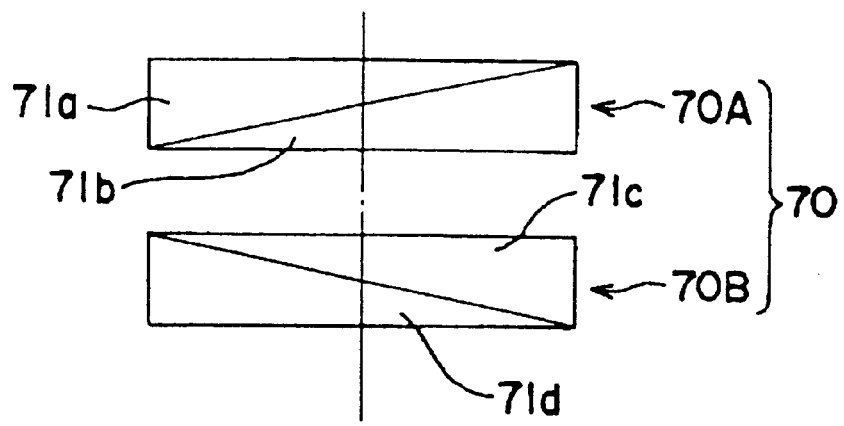
FIG. 23 is an enlarged side view showing the achromatic optical element shown in FIG. 21.
Figure 24:
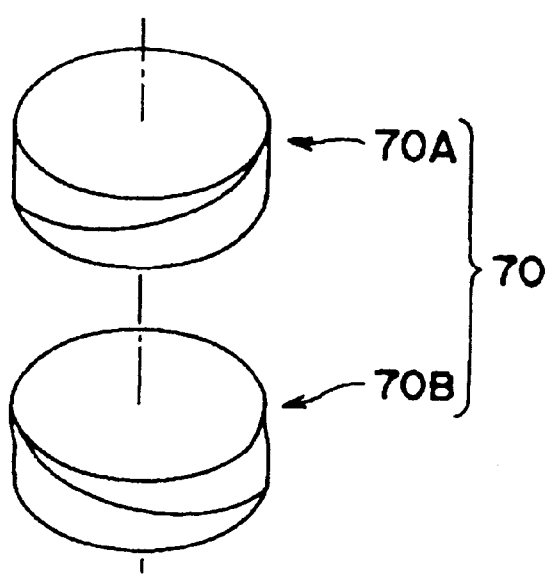
FIG. 24 is an enlarged perspective view showing the achromatic optical element shown in FIG. 21.

Here, the chromatic aberration canceling optical element 70 consists of a pair of variable prisms 70A and 70B as shown in FIGS. 23 and 24.

The variable prism 70A is constructed by bonding the prisms 71a and 71b and the variable prism 70B is constructed by bonding the prisms 71c and 71d. The prisms 71a and 71b, as well as the prisms 71c and 71d, have the same refractive index "nd" of a fundamental wavelength (d line). A dispersion ν of the prism 71a is smaller than a dispersion ν of the prism 71b. A dispersion ν of the prism 71d is smaller than a dispersion ν of the prism 71c. Here, the variable prisms 70A and 70B have the same structure.

Chromatic aberration is caused in a direction in which the refractive power of a prism acts. FIG. 22 shows a state in which reflected light from the back side of the drawing is refracted by optical members 60 and guided to an objective lens 19. Here, a state in which light beams with R, G, and B wavelengths are separated from each other by the optical members 60 is indicated. In the case where the chromatic aberration canceling optical element 70 is adjusted by its rotation such that respective light beams R', G', and B' become parallel light fluxes at the time when they are passed through the chromatic aberration canceling optical element 70, chromatic aberration due to a refractive action of the optical members 60 is removed.

Figure 8:
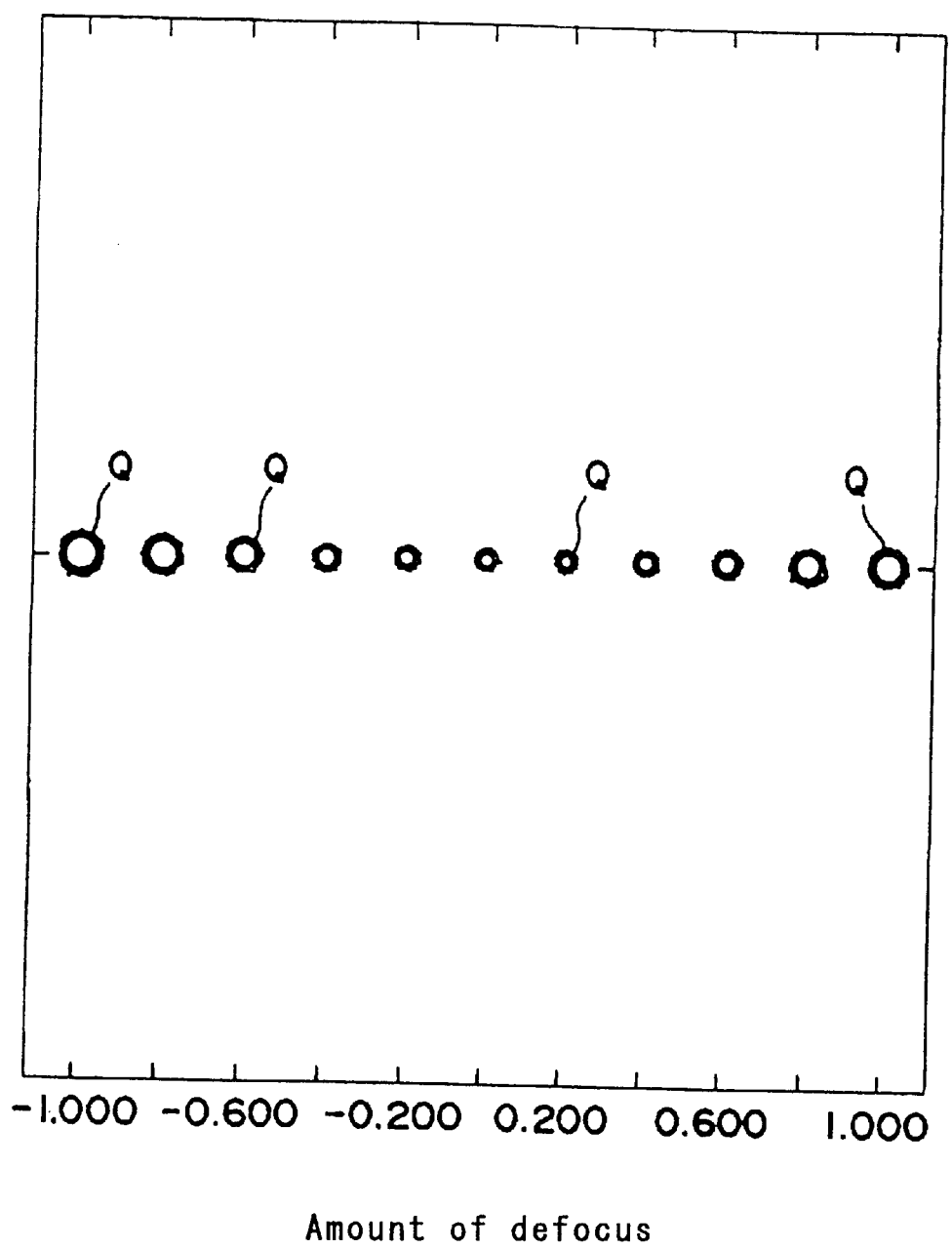
FIG. 8 is an explanatory diagram schematically showing a conventional relationship between the amount of defocus and a point image when no astigmatism is caused and chromatic aberration is considered.
Figure 9:
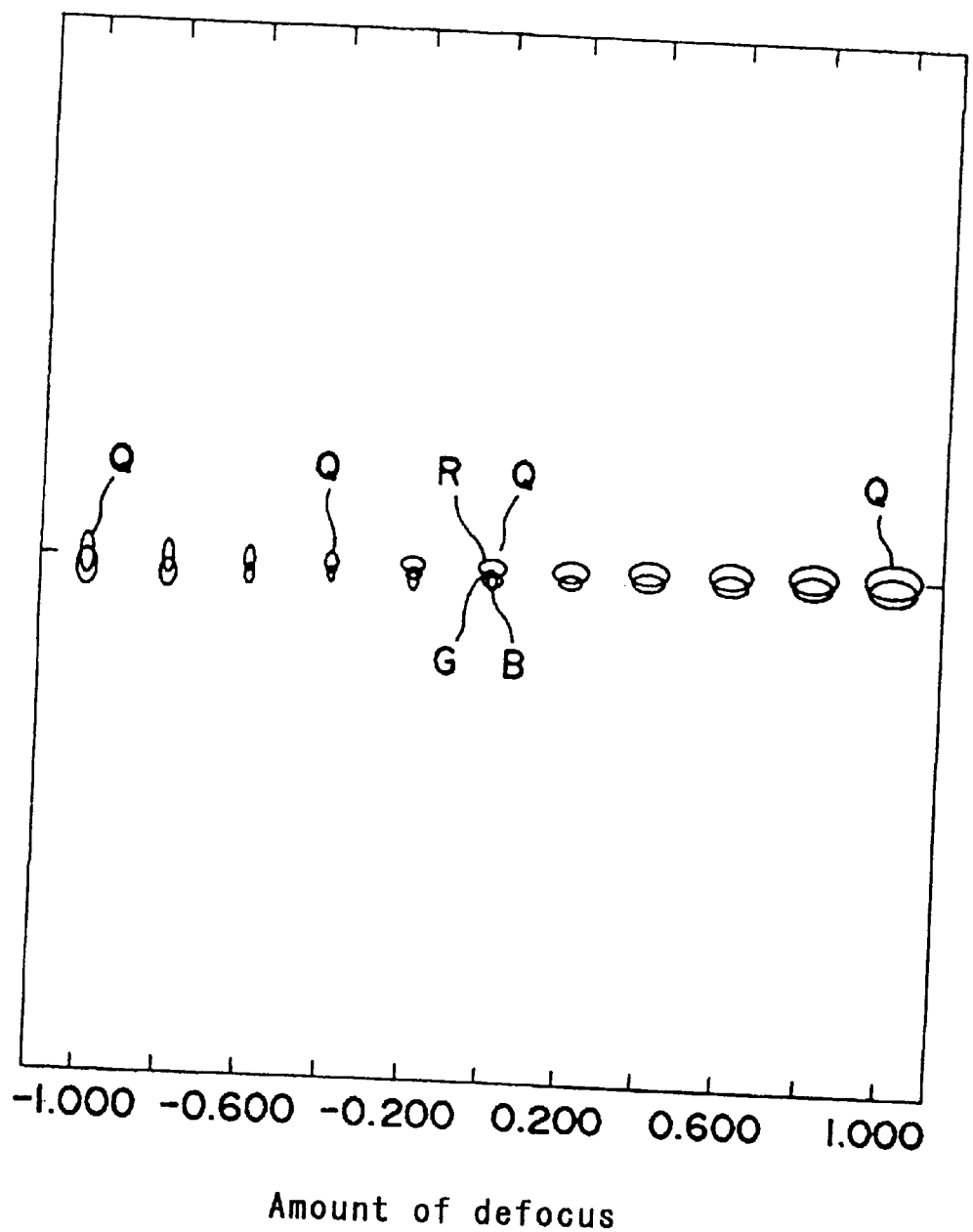
FIG. 9 is an explanatory diagram schematically showing a conventional relationship between the amount of defocus and a point image when it is assumed that astigmatism and chromatic aberration are caused.
Figure 10:
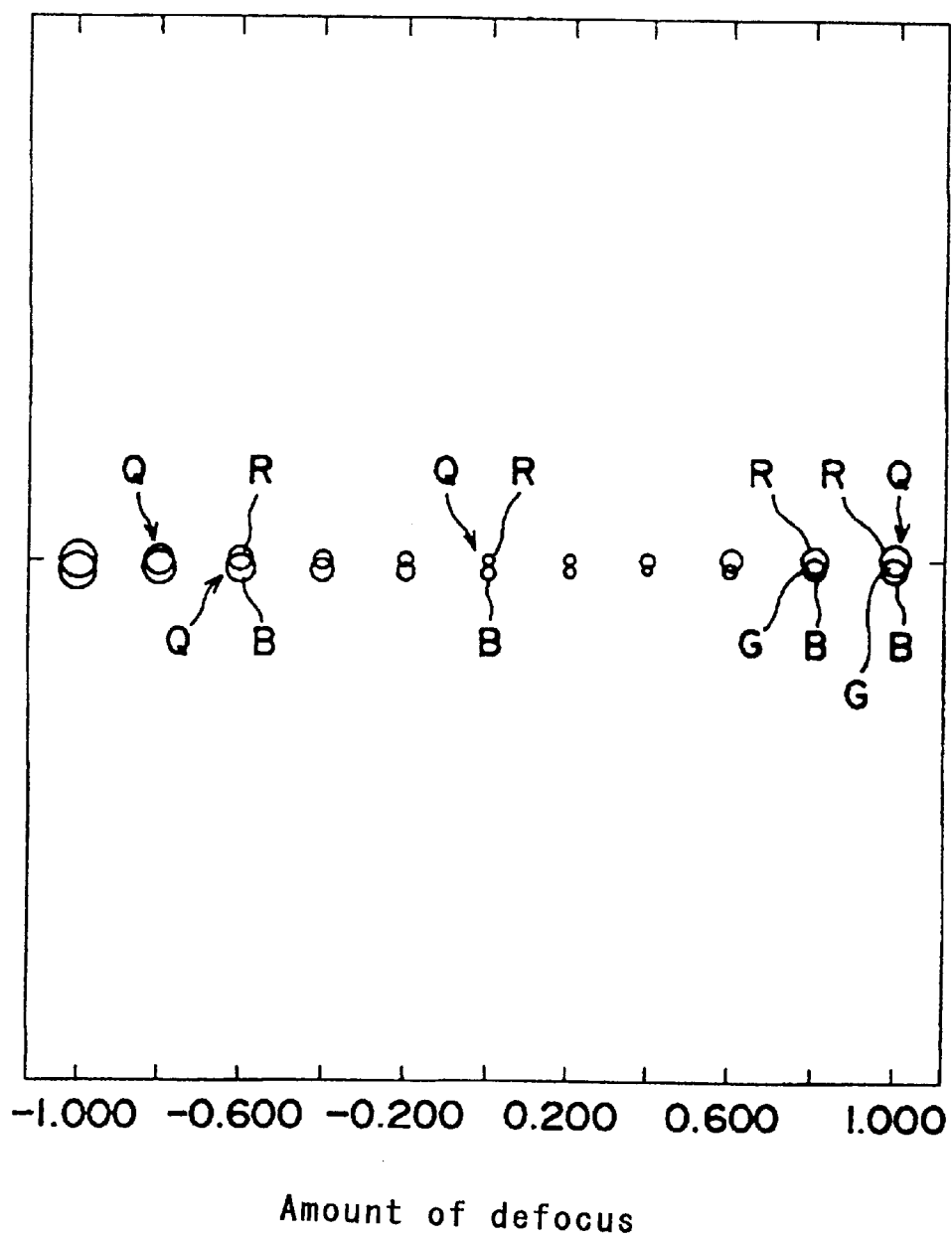
FIG. 10 is an explanatory diagram schematically showing a conventional relationship between the amount of defocus and a point image when astigmatism has been removed but chromatic aberration remains.
Figure 25:
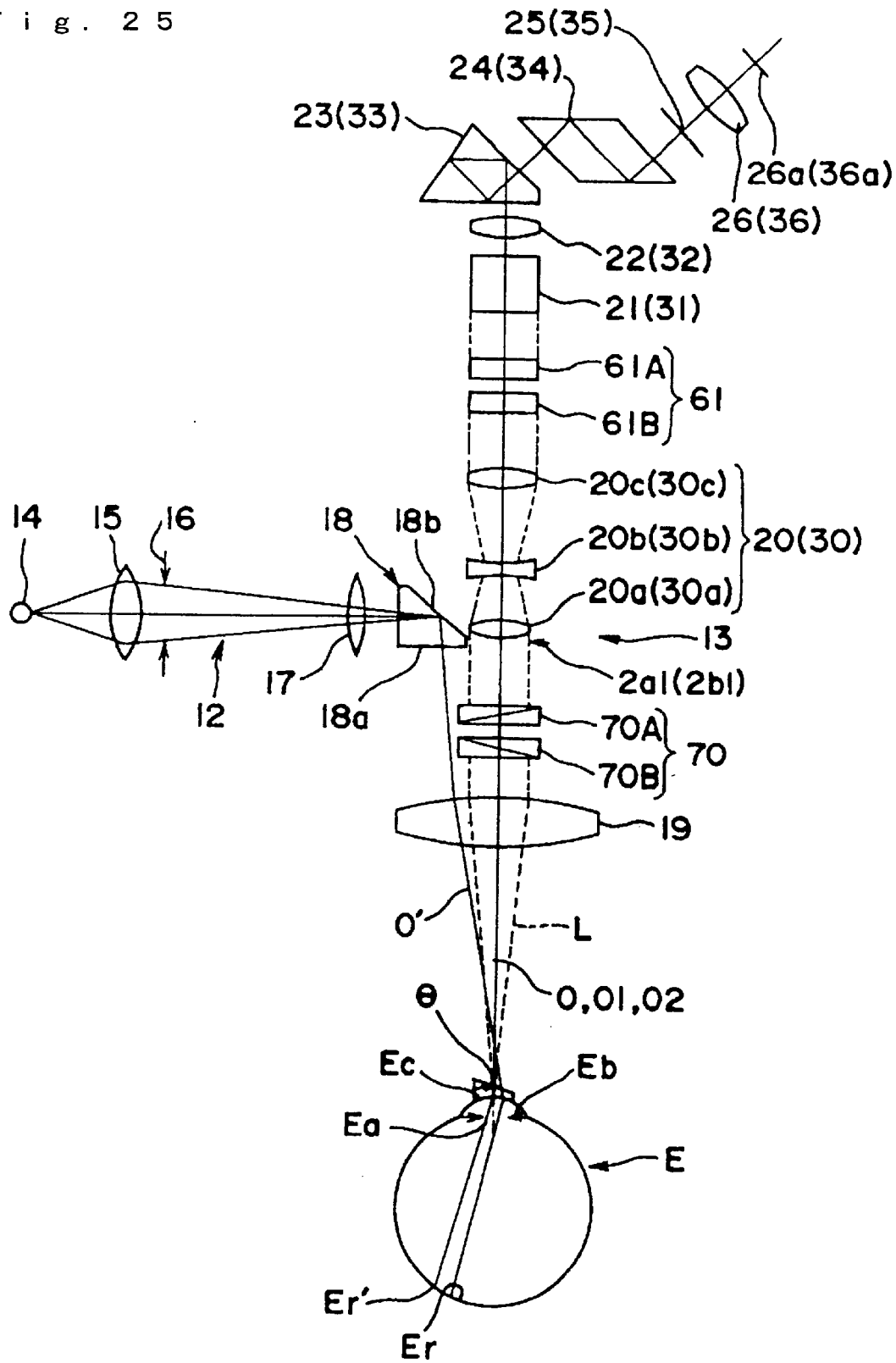
FIG. 25 shows an optical system in which an astigmatism canceling optical element and an achromatic optical element are provided on an observation path of an observation optical system.

Therefore, as shown in FIG. 25, an astigmatism canceling optical element 61 is located between the variable power lens system 20 (30) and an eyepiece 26 (36), and the chromatic aberration canceling optical element 71 is located between the objective lens 19 and the variable power lens system 20 (30). Then, when the astigmatism canceling optical element 61 is used, a point image with the astigmatism as shown in FIG. 9 can be corrected to a point image in which the astigmatism is removed to leave only the chromatic aberration as shown in FIG. 10. Next, when the chromatic aberration is corrected by using the chromatic aberration canceling optical element 70, the point image Q in which the astigmatism and the chromatic aberration are removed is obtained as shown in FIG. 8.

Embodiment 5

Figure 26:
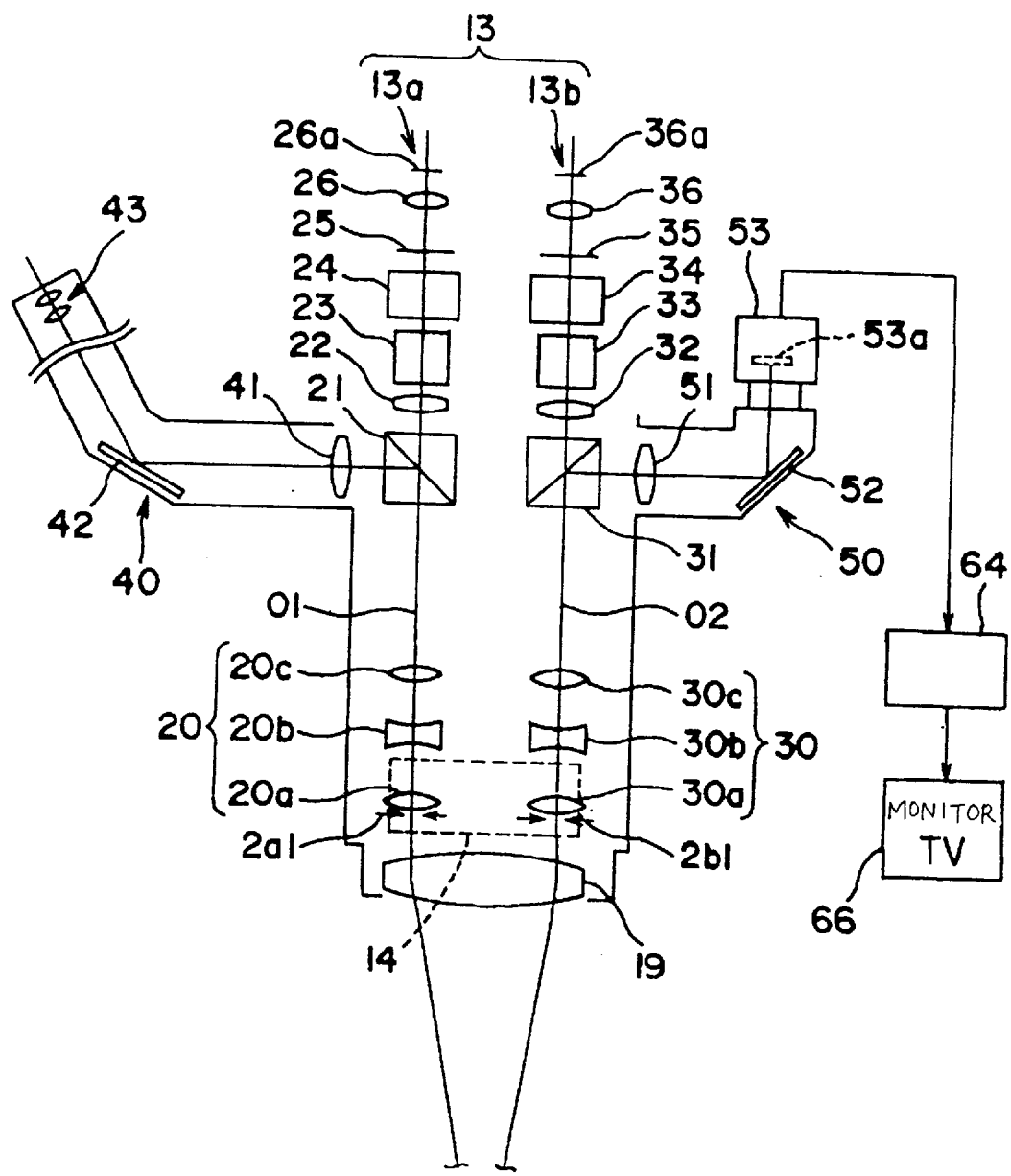
FIG. 26 is an optical configuration diagram showing Embodiment 5 of an observation apparatus according to the present invention.

FIG. 26 shows an optical system of Embodiment 5 of an observation apparatus according to the present invention. Here, an image processing device 64 includes a correction program as correction means for digitally analyzing chromatic aberration caused when the optical members 60 are held against an operating eye E and correcting it.

Figure 27:
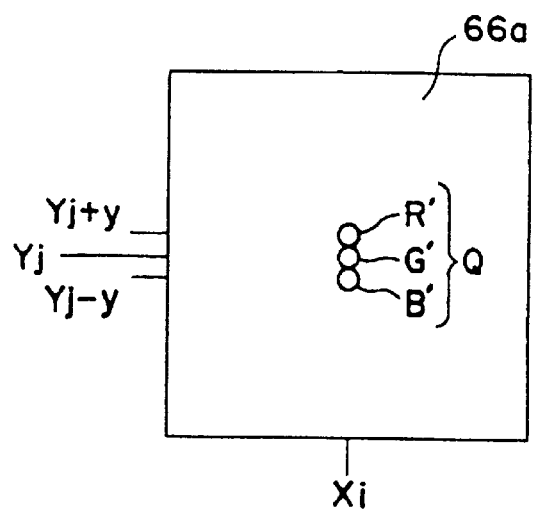
FIG. 27 shows using three point images of R, G, and B a typical example of a phenomenon whereby an image appears to be separated on a screen when chromatic aberration is caused.

When chromatic aberration is caused, as schematically shown in FIG. 27, a white point image Q is separated into three colors of R, G, and B so that point images R', G', and B' are obtained on a monitor screen 66a of a TV monitor 66.

Figure 28:
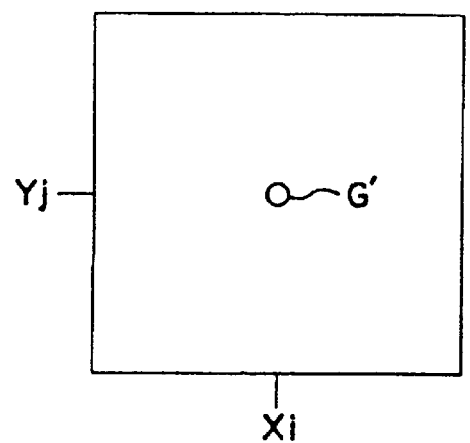
FIG. 28 is an explanatory view schematically showing a state in which only a layer of a G-image is extracted and stored.
Figure 29:
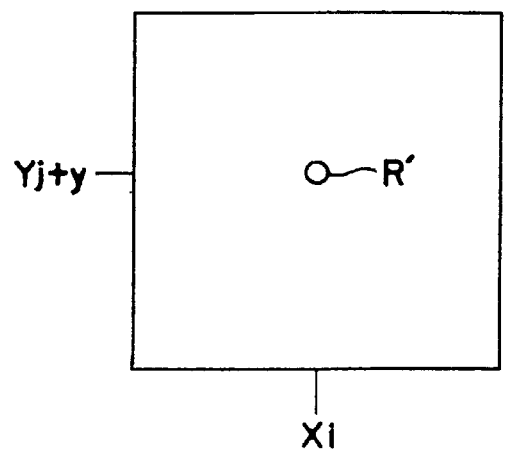
FIG. 29 is an explanatory view schematically showing a state in which only a layer of a R-image is extracted and stored.
Figure 30:
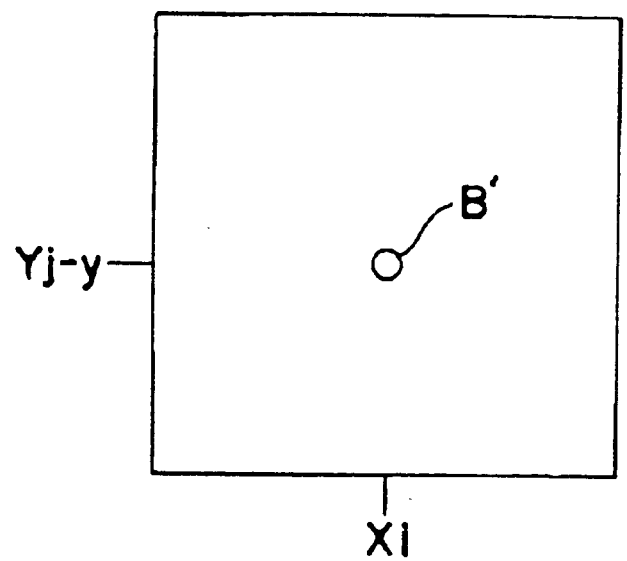
FIG. 30 is an explanatory view schematically showing a state in which only a layer of a B-image is extracted and stored.

The image shown in FIG. 27 is divided into respective layers of an R-layer, a G-layer, and a B-layer. An address of a corresponding pixel of the point image Q is stored for each of the layers. The image processing device 64 performs processing for overlapping, for example, the G layer for storing the point image G' at an address of Xi, Yj as shown in FIG. 28, the R layer for storing the point image R' at an address of Xi, Yj+y as shown in FIG. 29, and the B layer for storing the point image B' at an address of Xi, Yj−y as shown in FIG. 30.

Figure 31:
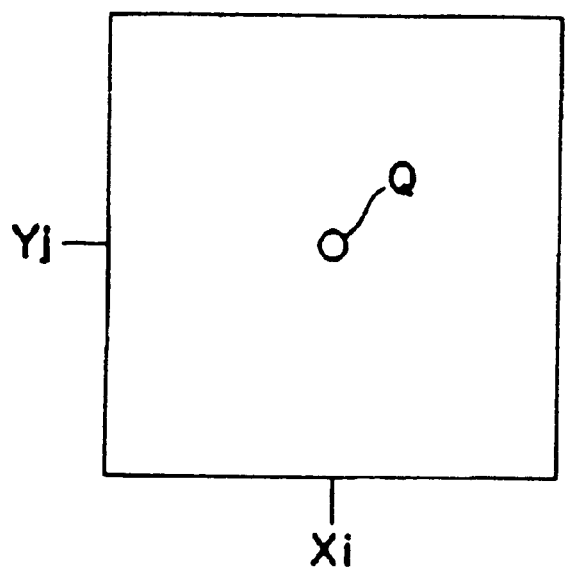
FIG. 31 is an explanatory view schematically showing a state in which the respective layers are overlapped with each other and displayed.

Thus, when the point images obtained by separating an image into three colors of R, G, and B on an image receiving element are digitally combined together at one point and chromatic aberration correction is conducted, even if an achromatic prism is not provided on observation optical systems 13a and 13b, achromatization can be digitally performed by software processing as shown in FIG. 31.

Embodiment 6

Figure 32:
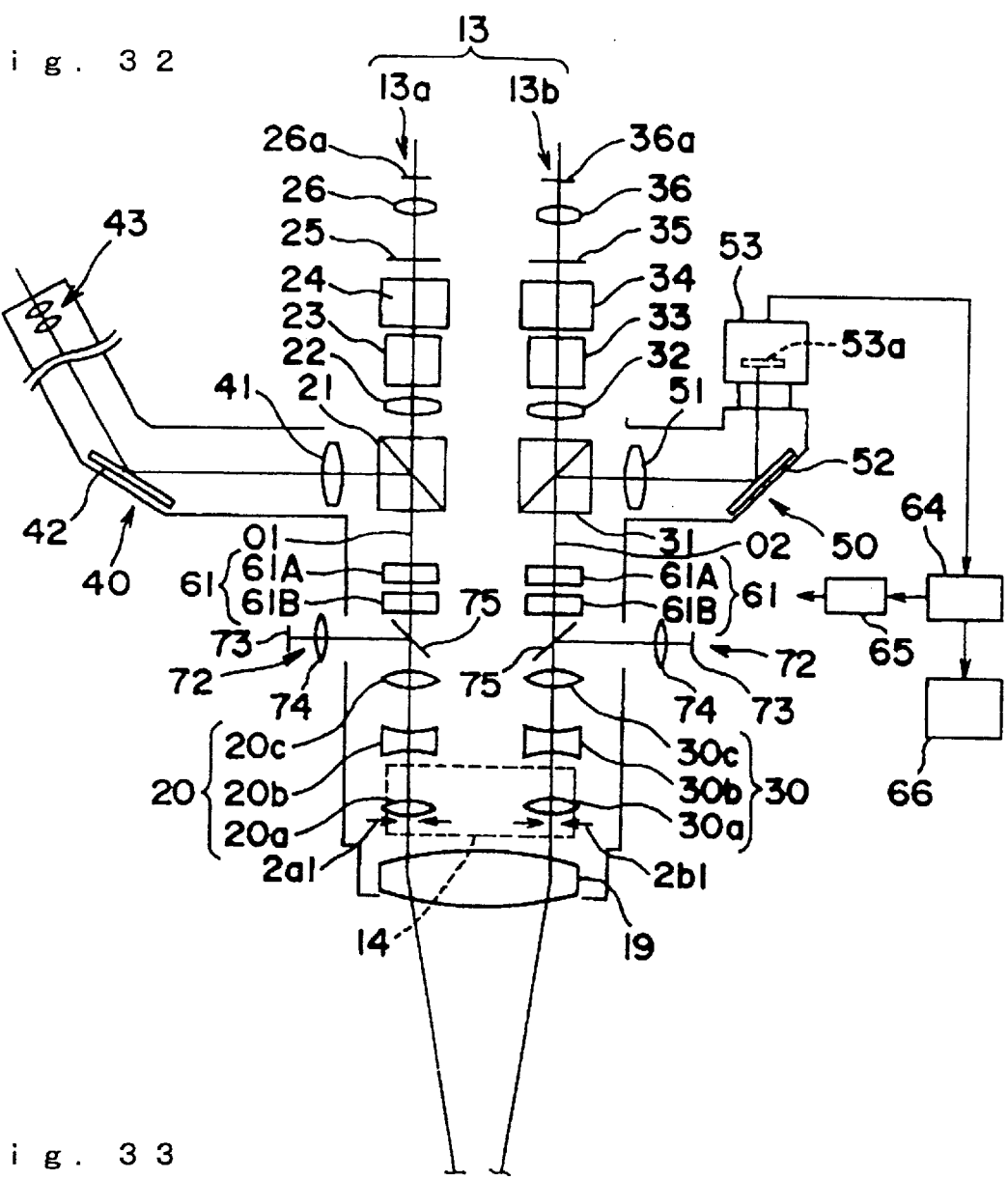
FIG. 32 is an explanatory view showing an optical system of Embodiment 6 of an observation apparatus according to the present invention.

FIG. 27 shows an optical system of Embodiment 6 of an observation apparatus according to the present invention. Here, projection optical systems 72 for projecting a pattern image to an eye fundus Er are provided between a variable power lens system 20 (30) and an astigmatism canceling optical element 61. Each projection optical system 72 (FIG. 32) consists of a ring-shaped pattern plate 73, a projective lens 74, and a half mirror 75. A ring-shaped pattern is guided to the optical members 60 via a variable power lens system 20 and an objective lens 19 and refracted by the optical members 60 to be guided to an eye fundus vicinity portion Er' of the eye fundus Er.

Figure 33:
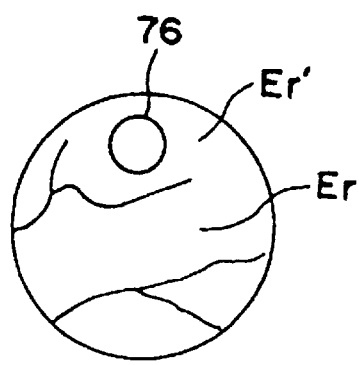
FIG. 33 shows a pattern image projected to an eye fundus vicinity portion by using a ring image projection system shown in FIG. 32.
Figure 34:
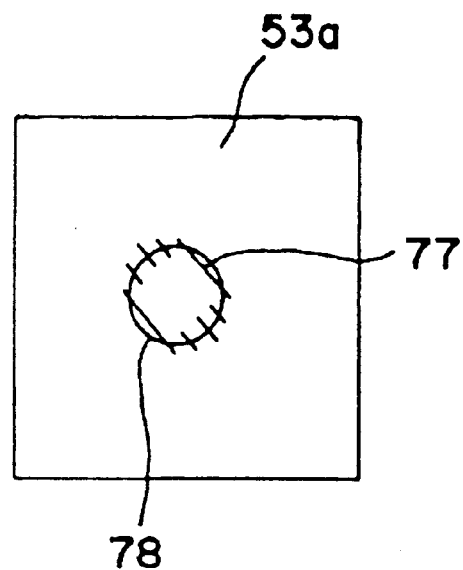
FIG. 34 is an explanatory view showing a state in which astigmatism is caused in a pattern image obtained on an image receiving element through a contact prism.

As shown in FIG. 33, a ring pattern image 76 is formed on the eye fundus vicinity portion Er'. When the ring pattern image is received on an image receiving element 53a in a state when the astigmatism canceling optical element 61 has no power, a ring pattern image 78 with a flow of image 77 resulting from astigmatism is obtained as shown in FIG. 34.

An image processing device 64 (FIG. 32) has analytic processing means for analyzing the ring pattern image 78, computes the amount of correction based on the flow of the ring pattern image 77, and outputs a drive signal to variable cylindrical lens rotating means 65 based on the computed result. The variable cylindrical lens rotating means 65 actuates in response to the drive signal the astigmatism canceling optical element 61 so as to cancel the astigmatism.

According to this Embodiment 6, the amount of astigmatism is computed based on a known ring image. Thus, the amount of astigmatism can be accurately determined.

As described above, the operation microscope has been described as examples of the observation apparatus in the foregoing embodiments of the present invention. However, the present invention is not limited to these and can be also applied to a slip lamp microscope and other ophthalmologic observation apparatuses.

Embodiment 7

Figure 35:
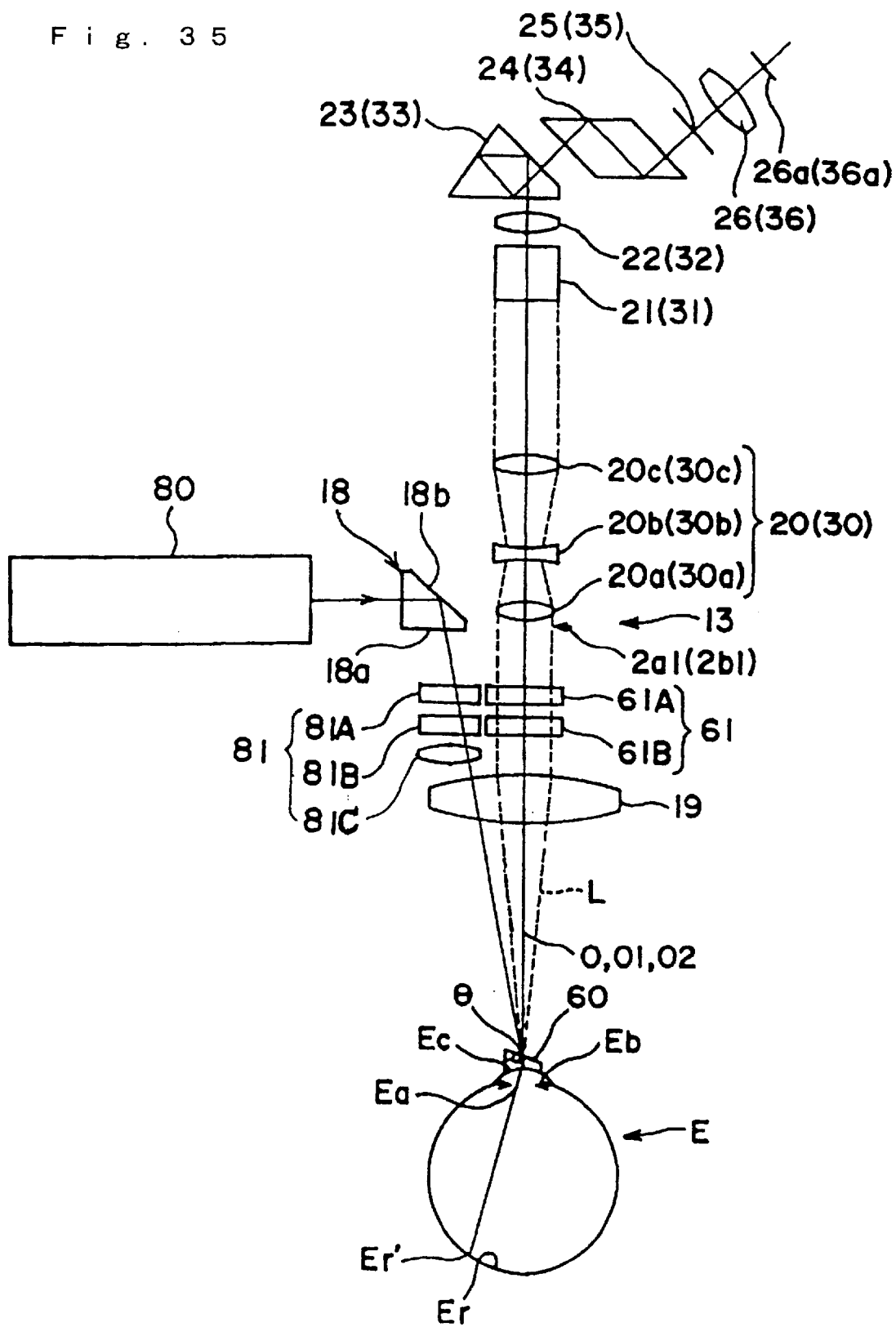
FIG. 35 shows an example of an observation apparatus including a therapeutic laser.

FIG. 35 is an optical configuration diagram for explaining Embodiment 7 of an observation apparatus according to the present invention. In FIG. 35, reference numeral 80 denotes a known irradiation optical system for irradiating therapeutic laser light to an eye fundus Er. The therapeutic laser light from the irradiation optical system 80 is relayed as a parallel fluxes by a colimate lens (not shown) and reflected by a prism 18 and guided to an objective lens 19.

An astigmatism canceling optical element 81 for canceling astigmatism caused when optical members 60 are held against an operating eye E and then therapeutic laser light is irradiated to the eye fundus Er through the optical members 60 are provided between the objective lens 19 and the prism 18. The astigmatism canceling optical element 81 is composed of variable cylindrical lenses 81A and 81B and a correction lens 81C as in Embodiment 1. A correction amount of astigmatism of variable cylinder lens 81 A, 81B, may be carried out too in a software processing of the correction amount to carry out an automatic correction.

According to such a configuration, when conducting laser therapy for the eye fundus Er whereby the optical members 60 are held against the operating eye E, astigmatism resulting from the presence of the optical members 60 can be removed.

According to the first to ninth aspects of the invention, the astigmatism caused when the contact prism is held against the operating eye to observe the eye fundus vicinity portion can be canceled. In addition, even if the laser light irradiation optical system is not in common use of the objective lens 19, the irradiation removing the astigmatism may become possible to be carried out by considering the irradiating angle of the laser light.

In particular, according to the second and third aspects of the invention, the astigmatism canceling optical element is provided on the observation path of the observation optical system through which reflected light fluxes are relayed in parallel. Thus, the astigmatism can be easily canceled.

More particularly, according to the third aspect of the invention, the astigmatism can be canceled regardless of a change in the observation magnification, thus allowing convenience in operation.

Also, according to the fifth to eighth aspects of the invention, the astigmatism can be automatically canceled, thus allowing convenience.

In particular, according to the sixth and seventh aspects of the invention, the astigmatism can be automatically corrected by analyzing an image, thus allowing convenience in operation.

More particularly, according to the seventh aspect of the invention, a pattern with a known shape can be projected to the eye fundus in order to perform astigmatism analysis. Thus, the analytical processing can be accurately performed.

Also, according to the eighth aspect of the invention, the astigmatism can be speedily corrected even when a contact prism having an apical angle different from the reference apical angle is held against the operating eye.

According to the ninth aspect of the invention, both the canceling of the astigmatism and the canceling of the chromatic aberration can be conducted.

According to the tenth to twelfth aspects of the invention, the chromatic aberration caused when the contact prism is held against the operating eye to observe the eye fundus vicinity portion can be canceled.

In particular, according to the eleventh and twelfth aspects of the invention, the achromatic optical element is provided on the observation path of the observation optical system through which reflected light fluxes are relayed in parallel. Thus, the astigmatism can be easily canceled.

According to the thirteenth aspect of the invention, even when the chromatic aberration canceling optical element is not provided on the observation path of the observation optical system, the chromatic aberration can be processed by software processing. In addition, the chromatic aberration can be canceled even without changing the configuration of the observation optical system.

According to the fourteenth aspect of the invention, the astigmatism can be canceled to allow therapeutic laser light to be irradiated to the eye fundus.

What is claimed is:

1. An observation apparatus, which comprises a variable power lens system and an imaging lens located on an observation path of the observation optical system extending from an objective lens to an eyepiece, in which:

of the observation optical system, an observation optical system extending from the objective lens to the variable power lens system is an observation path for relaying as parallel light fluxes reflected light from an eye fundus of an operating eye to the variable power lens system; and of the observation optical system, an observation optical system extending from the variable power lens system to the imaging lens is an observation path for relaying as parallel light fluxes the reflected light fluxes obtained through the variable power lens system to the imaging lens, wherein an astigmatism canceling optical element is provided on the observation path of the observation optical system extending from the objective lens to the eyepiece, for canceling astigmatism power caused when optical members are held against the operating eye.

2. An observation apparatus according to claim 1, wherein the astigmatism canceling optical element is provided between the variable power lens system and the imaging lens.

3. An observation apparatus according to claim 1, wherein the astigmatism canceling optical element is provided between the objective lens and the variable power lens system.

4. An observation apparatus according to claim 2 or 3, wherein the astigmatism canceling optical element consists of a pair of variable cylindrical lenses that are rotatable relative to each other about an observation optical axis of the observation path and further includes a correction lens for arbitrarily correcting the amount of positive or negative astigmatism.

5. An observation apparatus according to claim 4, further comprising amount-of-astigmatism-correction automatic changing means capable of correcting astigmatism that changes according to observation magnifications, wherein the amount-of-astigmatism-correction automatic changing means includes variable cylindrical lens rotating means for rotating the variable cylindrical lenses, and the variable cylindrical lens rotating means rotates, in order to cancel the astigmatism, the variable cylindrical lenses relative to each other about the observation optical axis in accordance with an amount of astigmatism correction to thereby change power thereof.

6. An observation apparatus according to claim 5, wherein the observation optical system further includes image receiving means for receiving reflected light from the eye fundus, the image receiving means being connected with an image processing device, and wherein the amount-of-astigmatism-correction automatic changing means computes the amount of astigmatism correction by analyzing an eye fundus image received on the image receiving means by the image processing device, and controls the variable cylindrical lens rotating means to rotate the variable cylindrical lenses in accordance with a computed result.

7. An observation apparatus according to claim 5, wherein the observation optical system further includes:
a projection optical system for projecting a pattern image to the eye fundus through the objective lens; and
image receiving means for receiving reflected light from the eye fundus, which is connected with an image processing device, and wherein the amount-of-astigmatism-correction automatic changing means computes the amount of astigmatism correction by analyzing a pattern image received on the image receiving means by using the image processing device, and controls the variable cylindrical lens rotating means to rotate the variable cylindrical lenses in accordance with a computed result.

8. An observation apparatus according to claim 5, wherein the amount-of-astigmatism-correction automatic changing means includes a memory for storing the amounts of astigmatism correction corresponding to respective observation magnifications of a prism having a reference apical angle, and wherein the amount-of-astigmatism-correction automatic changing means corrects, after once determining the amount of correction corresponding to an observation magnification of a prism having an apical angle different from that of the prism having the reference apical angle, the amounts of correction corresponding to other observation magnifications in accordance with the amounts of correction stored in the memory.

9. An observation apparatus according to claim 2 or 3, further comprising an achromatic optical element which is provided between the variable power lens system and the imaging lens and has power in a direction for canceling chromatic aberration caused when optical members are held against the operating eye.

10. An observation apparatus, which comprises a variable power lens system and an imaging lens located on an observation path of the observation optical system extending from an objective lens to an eyepiece, in which:

of the observation optical system, an observation optical system extending from the objective lens to the variable power lens system is an observation path for relaying as parallel light fluxes reflected light from an eye fundus of an operating eye to the variable power lens system; and of the observation optical system, an observation optical system extending from the variable power lens system to the imaging lens is an observation path for relaying as parallel light fluxes the reflected light fluxes obtained through the variable power lens system to the imaging lens, wherein an achromatic optical element is provided on the observation path of the observation optical system extending from the objective lens to the eyepiece, for canceling chromatic aberration caused when optical members are held against the operating eye.

11. An observation apparatus according to claim 10, wherein the achromatic optical element is provided between the variable power lens system and the eyepiece.

12. An observation apparatus according to claim 10, wherein the achromatic optical element is provided between the objective lens and the variable power lens system.

13. An observation apparatus, which comprises:

a variable power lens system and an imaging lens located on an observation path of the observation optical system extending from an objective lens to an eyepiece, in which:

of the observation optical system, an observation optical system extending from the objective lens to the variable power lens system is an observation path for relaying as parallel light fluxes reflected light from an eye fundus of an operating eye to the variable power lens system;

of the observation optical system, an observation optical system extending from the variable power lens system to the imaging lens is an observation path for relaying as parallel light fluxes the reflected light fluxes obtained through the variable power lens system to the imaging lens; and the observation optical system includes image receiving means for receiving the reflected light from the eye fundus and displaying an eye fundus image, the image receiving means being connected with an image processing device, wherein the image processing device includes, in order to correct the chromatic aberration caused when optical members are held against the operating eye, chromatic aberration correcting means for correcting chromatic aberration by digitally combining at one point point images that are obtained by separating an image into three colors of R, G, and B on the image receiving means.

14. An observation apparatus, which comprises a variable power lens system and an imaging lens located on an observation path of the observation optical system extending from an objective lens to an eyepiece, in which:

of the observation optical system, an observation optical system extending from the objective lens to the variable power lens system is an observation path for relaying as parallel light fluxes reflected light from an eye fundus of an operating eye to the variable power lens system; and of the observation optical system, an observation optical system extending from the variable power lens system to the imaging lens is an observation path for relaying as parallel light fluxes the reflected light fluxes obtained through the variable power lens system to the imaging lens; and eye fundus therapy is performed by using an irradiation optical system for irradiating therapeutic laser light, wherein an astigmatism canceling optical element is provided for canceling astigmatism caused when optical members are held against the operating eye to irradiate the therapeutic laser light to the eye fundus.

* * * * *

(12) EX PARTE REEXAMINATION CERTIFICATE (5948th)
United States Patent
Fukuma et al.

(10) Number: US 6,726,326 C1
(45) Certificate Issued: Oct. 16, 2007

(54) OBSERVATION APPARATUS

(75) Inventors: Yasufumi Fukuma, Tokyo (JP); Hidetaka Aeba, Tokyo (JP)

(73) Assignee: Kabushiki Kaisha Topcon, Itabashi-Ku, Tokyo (JP)

Reexamination Request:
No. 90/007,973, Mar. 10, 2006

Reexamination Certificate for:
Patent No.: 6,726,326
Issued: Apr. 27, 2004
Appl. No.: 10/309,309
Filed: Dec. 4, 2002

(30) Foreign Application Priority Data

Dec. 5, 2001 (JP) .................................. 2001-371536

(51) Int. Cl.
*A61B 3/10* (2006.01)

(52) U.S. Cl. ...................................................... 351/216
(58) Field of Classification Search .................. None
See application file for complete search history.

(56) References Cited

U.S. PATENT DOCUMENTS

| | | | |
|---|---|---|---|
| 3,915,564 A | 10/1975 | Urban | 351/7 |
| 4,452,517 A | 6/1984 | Kohayakawa | 351/206 |
| 4,601,550 A | 7/1986 | Yoshino et al. | 350/516 |
| 4,679,919 A | 7/1987 | Itoh et al. | 351/206 |
| 5,098,426 A | 3/1992 | Sklar et al. | 606/5 |
| 5,490,849 A | 2/1996 | Smith | 606/5 |
| 5,615,278 A | 3/1997 | Matsumoto | 382/128 |
| 5,877,900 A | 3/1999 | Omura | 359/644 |
| 5,943,116 A | 8/1999 | Zeimer | 351/221 |
| 6,033,396 A | 3/2000 | Huang et al. | 606/5 |
| 6,304,723 B1 | 10/2001 | Kohayakawa | 396/18 |

FOREIGN PATENT DOCUMENTS

| | | |
|---|---|---|
| DE | 2202120 | 7/1973 |
| DE | 3546915 | 8/1999 |
| JP | 3-43623 | 4/1991 |
| JP | 5-20723 | 3/1993 |
| JP | 06-142052 | 5/1994 |
| JP | 06-267820 | 9/1994 |
| JP | 07-016253 | 1/1995 |
| JP | 10-221607 | 8/1998 |
| JP | 10-254053 | 9/1998 |
| JP | 2001-108906 | 4/2001 |

*Primary Examiner*—Beverly M. Flanagan

(57) ABSTRACT

An observation apparatus capable of removing astigmatism is provided. The observation apparatus includes a variable power lens system (20) located on an observation path of an observation optical system (13a) extending from an objective lens (19) to an imaging lens (22). A portion of the observation optical system which extends from the objective lens (19) to the variable power lens system (20) serves an as observation path through which reflected light fluxes from an eye fundus (Er) of an operating eye (E) are relayed to the variable power lens system (20) as parallel light fluxes. A portion thereof which extends from the variable power lens system (20) to the imaging lens (22) serves as an observation path through which the reflected light fluxes obtained through the variable power lens system (20) are relayed to an eyepiece (26) as parallel light fluxes. An astigmatism canceling optical element (61) for canceling astigmatism power caused when optical members (60) are held against the operating eye (E) is provided in any location on the observation path of the observation optical system (13a) extending from the objective lens (19) to the eyepiece (26).

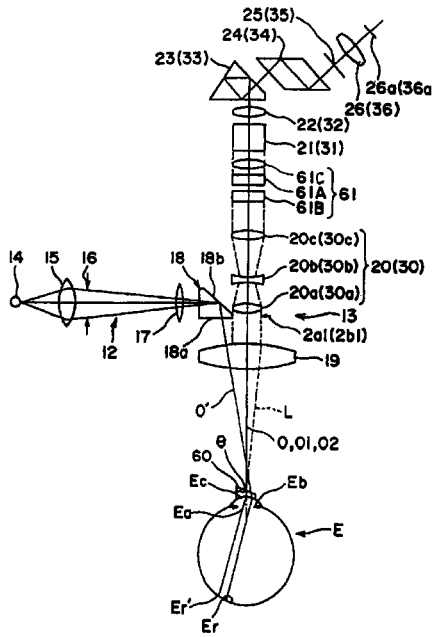

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 10–14 is confirmed.

Claims 1–5 are determined to be patentable as amended.

Claims 6–9, dependent on an amended claim, are determined to be patentable.

1. An observation apparatus, which comprises a variable power lens system (20) and an imaging lens (22) located on an observation path of the observation optical system (13A) extending from an objective lens (19) to an eyepiece (26) in which:
   a portion of the observation optical system *extending from the objective lens (19) to the variable power lens system (20) is*, an observation [optical system extending from the objective lens to the variable power lens system is an observation] path for relaying as parallel light fluxes reflected light from an eye fundus (Er) of an operating eye (E) to the variable power lens system; and
   a portion of the observation optical system *extending from the variable power lens system (20) to the imaging lens (22) is*, an observation [optical system extending from the variable power lens system to the imaging lens is an observation ] path for relaying as parallel light fluxes the reflected light fluxes obtained through the variable power lens system (20) to the imaging lens,
   [wherein an astigmatism canceling optical element is] *a pair of variable cylindrical lenses (61)* provided on the observation path of the observation optical system extending from the objective lens to the eyepiece[, for canceling astigmatism power caused when optical members are held against the operating eye] *(26) and is rotatable relative to each other about an observation optical axis of the observation path, for canceling astigmatism caused when a prism (60) is held against the operating eye (E), a memory (69) for storing the amounts of astigmatism correction corresponding to respective observation magnifications of a reference prism (60) having a reference apical angle (θ);*
   *wherein the amount of correction required for canceling astigmatism when another prism having an optical angle different from the reference apical angle (θ) is held while observing the fundus against the operating eye with a first value of the observation magnification is adapted to be settable by an operator,*
   *means (64) for, when the observation magnification of the another prism is changed from the first value to a second value in response to an input from the operator, computing a ratio fo the amount of correction of the reference prism with the first value based on the amounts of astigmatism correction stored in the memory, and*
   *rotating means (65) for rotating the pair of variable cylindrical lenses based on the computer amount of correction of the another prism with the second value.*

2. An observation apparatus according to claim 1, wherein the [astigmatism canceling optical element] *pair of variable cylindrical lenses* is provided between the variable power lens system and the imaging lens.

3. An observation apparatus according to claim 1, wherein the [astigmatism canceling optical element] *pair of variable cylindrical lenses* is provided between the objective lens and the variable power lens system.

4. An observation apparatus according to claim 2 or 3, [wherein the astigmatism canceling optical element consists of a pair of variable cylindrical lenses that are rotatable relative to each other about an observation optical axis of the observation path and further includes a correction lens for arbitrarily correcting the amount of positive or negative astigmatism] *further comprising an achromatic optical element which is provided between the objective lens to the variable lens and has power in a direction for canceling chromatic aberration caused when the prism is held against the operating eye.*

5. An observation apparatus according to claim [4] *1*, further comprising [amount-of-astigmatism-correction automatic changing means capable of correcting astigmatism that changes according to observation magnifications,
   wherein the amount-of-astigmatism-correction automatic changing means includes variable cylindrical lens rotating means for rotating the variable cylindrical lenses, and the variable cylindrical lens rotating means rotates, in order to cancel the astigmatism, the variable cylindrical lenses relative to each other about the observation optical axis in accordance with an amount of astigmatism correction to thereby change power thereof] *an irradiation optical system (80) for irradiating therapeutic laser light for performing eye fundus therapy, and an astigmatism canceling optical element (81) for canceling astigmatism caused when the prism is held against the operating eye and the therapeutic laser light is irradiated to the eye fundus.*

* * * * *